(12) United States Patent
Mazess et al.

(10) Patent No.: US 6,517,487 B1
(45) Date of Patent: Feb. 11, 2003

(54) ULTRASONIC DENSITOMETER WITH OPPOSED SINGLE TRANSDUCER AND TRANSDUCER ARRAY

(75) Inventors: Richard B. Mazess, Madison; Scott A. Wiener, Mount Horeb; Richard F. Morris, Stoughton, all of WI (US)

(73) Assignee: Lunar Corporation, Madison, WI (US)

( * ) Notice: Subject to any disclaimer, the term of this patent is extended or adjusted under 35 U.S.C. 154(b) by 0 days.

(21) Appl. No.: 09/357,631

(22) Filed: Jul. 20, 1999

Related U.S. Application Data

(63) Continuation-in-part of application No. 09/094,073, filed on Jun. 9, 1998, now Pat. No. 6,027,449, which is a continuation-in-part of application No. 08/795,023, filed on Feb. 4, 1997, now Pat. No. 6,012,779, which is a continuation-in-part of application No. 08/466,495, filed on Jun. 6, 1995, now Pat. No. 5,603,325, which is a continuation-in-part of application No. 08/397,027, filed on Mar. 1, 1995, now Pat. No. 5,483,965.

(51) Int. Cl.[7] .................................................. A61B 8/00
(52) U.S. Cl. ...................................................... 600/449
(58) Field of Search ............................... 600/437–438, 600/442, 443, 449; 73/597, 599

(56) References Cited

U.S. PATENT DOCUMENTS

| | | | |
|---|---|---|---|
| 4,105,018 A | 8/1978 | Greenleaf et al. ............. 73/597 |
| 4,138,999 A | 2/1979 | Eckhart et al. ......... 128/661.03 |
| 4,217,912 A | 8/1980 | Hubmann et al. .......... 128/774 |
| 4,233,845 A | 11/1980 | Pratt, Jr. .................... 73/865.4 |
| 4,235,243 A | 11/1980 | Saha .......................... 128/740 |
| 4,237,901 A | 12/1980 | Taenzer ...................... 128/660 |
| 4,250,895 A | 2/1981 | Lees ........................... 178/776 |
| 4,316,183 A | 2/1982 | Palmer et al. .............. 340/621 |
| 4,361,154 A | 11/1982 | Pratt, Jr. ................. 128/660.01 |
| 4,421,119 A | 12/1983 | Pratt, Jr. ................. 128/661.01 |
| 4,476,873 A | 10/1984 | Sorenson et al. ...... 128/661.01 |
| 4,483,343 A | 11/1984 | Beyer et al. ................ 128/660 |
| 4,517,840 A | 5/1985 | Thompson et al. ........... 73/644 |
| 4,522,068 A | 6/1985 | Smith ......................... 73/32 A |
| 4,530,360 A | 7/1985 | Duarte ........................ 128/419 |
| 4,597,292 A | 7/1986 | Fujii et al. .................... 73/599 |
| 4,669,482 A | 6/1987 | Ophir .................... 128/661.03 |
| 4,774,959 A | 10/1988 | Palmer .................. 128/660.06 |

(List continued on next page.)

FOREIGN PATENT DOCUMENTS

| | | |
|---|---|---|
| EP | 0045265 A | 2/1982 |
| EP | 0585492 A1 | 3/1994 |
| GB | 2 309 083 | 2/1998 |
| WO | WO 95/26160 | 10/1995 |
| WO | WO 96/03080 | 2/1996 |

OTHER PUBLICATIONS

C.Rich, E.Klink, R.Smith, B.Graham, P. Ivanovich, *Sonic Measurement of Bone Mass*, Progress in Development of Methods in Bone Densitometry, pp. 137–146, (NASA 1966).

(List continued on next page.)

*Primary Examiner*—Francis J. Jaworski
(74) *Attorney, Agent, or Firm*—Quarles & Brady LLP

(57) ABSTRACT

A scanning ultrasonic apparatus provides measurements of a bone at a number of spatially separated locations. These measurements may produce an image or may be used to automatically identify a measurement region of interest or to align a series of measurements with each other despite possible shifting in the bony member in between measurements.

13 Claims, 13 Drawing Sheets

U.S. PATENT DOCUMENTS

| | | | |
|---|---|---|---|
| 4,913,157 A | 4/1990 | Pratt et al. | 128/661.03 |
| 4,930,511 A * | 6/1990 | Rossman et al. | 600/437 |
| 5,014,970 A | 5/1991 | Osipov | 269/328 |
| 5,042,489 A | 8/1991 | Wiener | 128/661.03 |
| 5,095,907 A | 3/1992 | Kudo et al. | 128/660 |
| 5,119,820 A | 6/1992 | Rossman et al. | 128/661.03 |
| 5,134,999 A | 8/1992 | Osipov | 128/661.03 |
| 5,143,069 A | 9/1992 | Kwon et al. | 128/660.01 |
| 5,218,963 A | 6/1993 | Mazess | 128/661.03 |
| 5,259,384 A | 11/1993 | Kaufman et al. | 128/660.06 |
| 5,309,898 A | 5/1994 | Kaufman et al. | 601/2 |
| 5,335,661 A | 8/1994 | Koblanski | 128/661.03 |
| 5,348,009 A | 9/1994 | Ohtomo et al. | 128/661.03 |
| 5,349,959 A | 9/1994 | Wiener et al. | 128/661.03 |
| 5,452,722 A | 9/1995 | Langton | 128/661.03 |
| 5,458,130 A | 10/1995 | Kaufman et al. | 128/661.03 |
| 5,547,459 A | 8/1996 | Kaufman et al. | 601/2 |
| 5,603,325 A | 2/1997 | Mazess et al. | 128/660.06 |
| 5,615,681 A | 4/1997 | Ohtomo | 128/661 |
| 5,651,363 A | 7/1997 | Kaufman et al. | 128/660.02 |
| 5,729,660 A | 3/1998 | Chiabrera et al. | 395/22 |
| 5,752,924 A | 5/1998 | Kaufman et al. | 601/2 |
| 5,770,801 A | 6/1998 | Wang et al. | 73/644 |
| 5,772,596 A * | 6/1998 | Forfitt et al. | 600/449 |
| 5,774,631 A | 6/1998 | Chiabrera et al. | 395/22 |
| 5,782,763 A | 7/1998 | Bianco et al. | 600/407 |
| 5,785,656 A | 7/1998 | Chiabrera et al. | 600/449 |
| 5,806,520 A * | 9/1998 | Berger et al. | 600/449 |
| 5,879,301 A * | 3/1999 | Chiabrera et al. | 600/437 |

OTHER PUBLICATIONS

M.Greenspan, C.E.Tschiegg, *Sing–Around Ultrasonic Velocimeter for Liquids*, The Review of Scientific Instruments, vol. 28, No. 11, pp. 897–901 (1957).

W.Abendschein and G.W. Hyatt, *Ultrasonics and Selected Physical Properties of Bone*,.Clinical Orthopedics and Related Research, No. 69, pp. 294–301 (1970).

M.Gerlanc, D.Haddad, G.Hyatte, J.Langloh, P.St.Hilaire, *Ultrasonic Study of Normal and Fractured Bone*, Clinical Orthopedics and Related Research, pp. 175–180, (1975).

B. Martin, R.R.Haynes, *The Relationship Between the Speed of Sound and Stiffness of Bone*, Biomechanics Laboratories, West Virginia University (1970).

J.M.Hoop, W.N.Clotfelter, *Ultrasonic Bone Density Measurements*, Marshall Space Flight Center, The Fall Conference of the American Society for Nondestructive Testing (1970).

K.H. Okumura, *Preventative Diagnosis of Breakdown*, Massachusetts Institute of Technology (1978).

W.N.McDicken, *The Physics of Ultrasound in Diagnostic Ultrasonics*, pp. 35–61 (1976).

S.Lees, C. Davidson, The role of Collagen in the Elastic Processes of Calcified Tissues, C. Journal of Biomechanics, vol. 10, No. 7 (1977) pp. 473–486.

G. Van Venrooij, *Measurement of Ultrasound Velocity in Human Tissue*, Ultraonsics, Oct. (1971), pp. 24–242.

S. Lang, Ultrasonic Method for Measuring Elastic Coefficients of Bone and Results on Fresh and Dried Bovine Bones, IEEE Transactions on Bio–Medical and Engineering, vol. BME–17, No. 2 (Apr. 1970), pp. 101–105.

B. Martin, R. Haynes, *The Investigation of Bone's Substructure Using Megahertz Sound and a Porous Model*, ASME Publication (Dec. 3, 1970).

S. A. Brown, M. B. Mayor, Ultrasonic Prediction of Delayed or Nonunion of Fractures, Proceedings of the Fifth New England Bioengineering Conference, (Apr. 15, 1997), pp. 229–233.

S. A. Brown, M. B. Mayor, Ultrasonic Assessment of Early Callus Formation, Biomedical Engineering, vol. 11, No. 4 (Apr. 1976), pp. 124–128.

H. Yamada, *Strength of Biological Materials*, pp. 53–57, (1970).

P. N. T. Wells, *Physical Principals of Ultrasonic Diagnosis*, Academic Press, London (1969), pp. 1–27.

B. S. Mather, Comparison of Two Formulae in Vivo Prediction of Strength of the Femur, Aeorspace Medicine, vol. 38, No. 12 (Dec. 1967), pp. 1270–1272.

P.J. Rossman, Measurements of Ultrasonic Velocity and Attenuation in the Human Os Calcis and Their Relationship Photon Absorptiometry Bone Mineral Measurements, Master's Thesis, Unversity of Wisconsin–Madison, 1987.

C.M. Langton, et al., A Contact Method for the Assessment of Ultrasonic Velocity and Broadband Attenuation in Cortical and Cencellous Bone, Clin. Phys. Physiol. Meas., 1990 vol. 11, No. 3, 243–249, Printed in UK.

J. Lawrence Katz, et al., The Structure and Anisotropic Mechanical Properties of Bone, IEEE Transactions on Biomedical Engineering BME–31 (1984) Dec., No. 12, New York, USA.

Robert E. Holm, et al., Use Discrete Fourier Transforms to Simplify Signal Processing, EDN (Apr. 1983).

V.Poll et al., Broadband Ultrasonic Attenuation in the os calcis and Single Photon Absorptiometry in the Distal Forearm: a Comparative Study, Clin. Phys. Physiol. Meas. 1986, vol. 7, No. 4, 375–379, Printed in Great Britain.

Shailendra S. Shukla et al., A Study of the Homegeneity of the Trabecular Bone Mineral Denisty, Med. Phys. 14(4) Jul./Aug. 1987.

George T. Anast, et al., Ultrasonic Technique for the Evaluation of Bone Fractures, Biol., Eng. Soc. vol. 11, No. 4, Apr. 176.

* cited by examiner

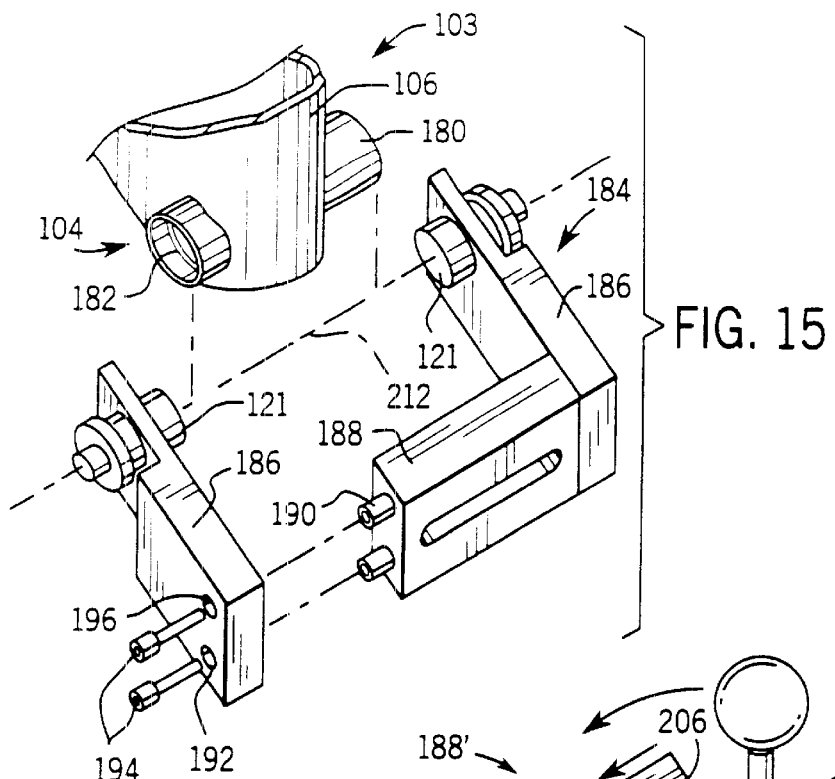
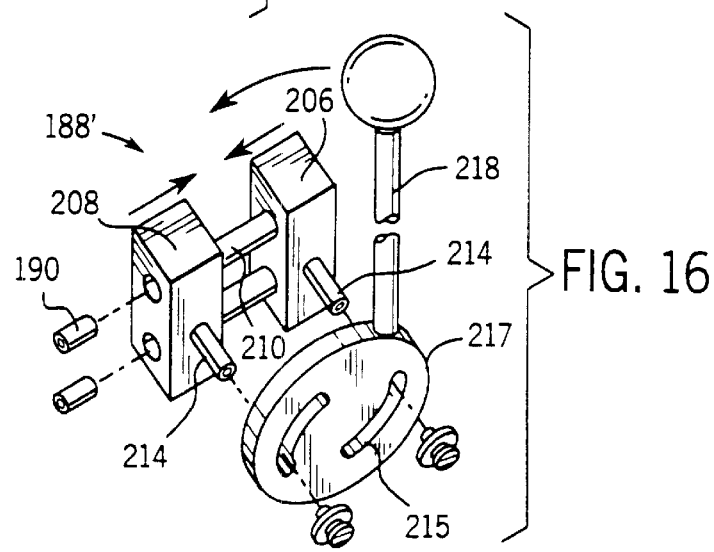
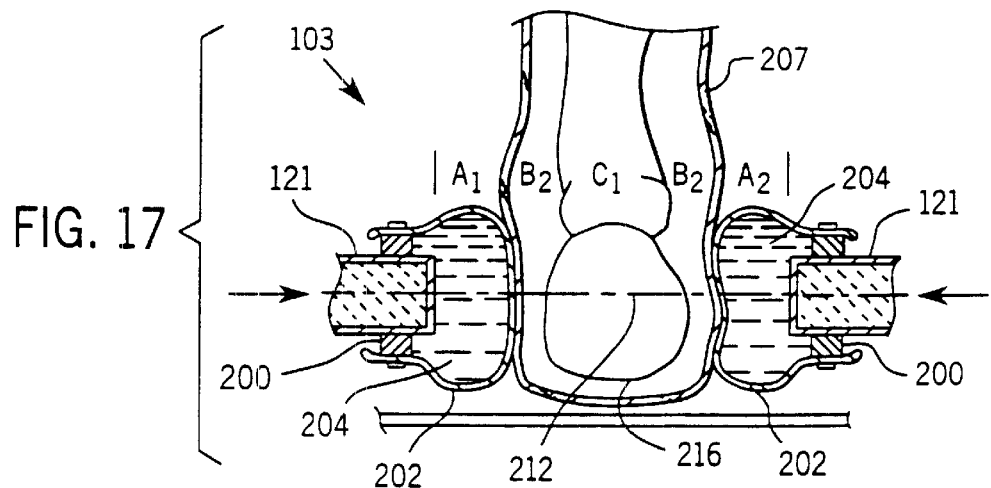

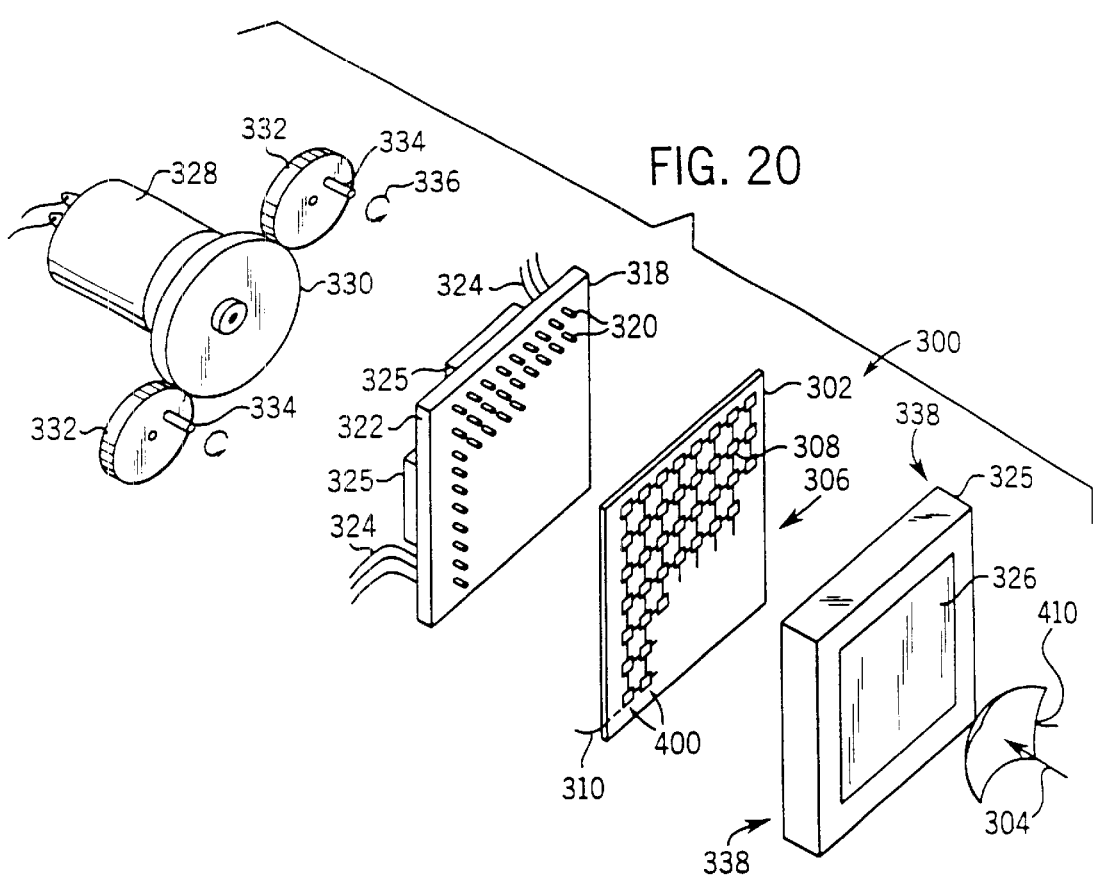
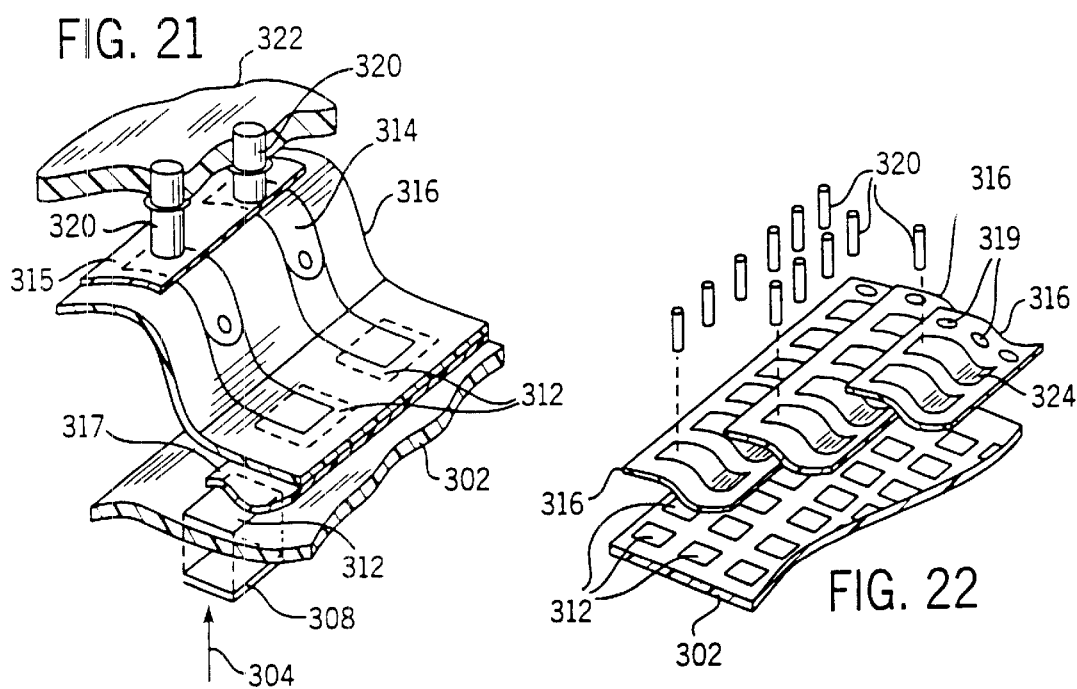

ULTRASONIC DENSITOMETER WITH OPPOSED SINGLE TRANSDUCER AND TRANSDUCER ARRAY

CROSS-REFERENCE TO RELATED APPLICATIONS

This application is a continuation-in-part of Ser. No. 09/094,073, filed Jun. 9, 1998, now U.S. Pat. No. 6,027,449, which is a continuation-in-part of Ser. No. 08/795,023, filed Feb. 4, 1997, now U.S. Pat. No. 6,012,779, which is a continuation-in-part of Ser. No. 08/466,495, filed Jun. 6, 1995, now U.S. Pat. No. 5,603,325, which is a continuation-in-part of Ser. No. 08/397,027, filed Mar. 1, 1995, now U.S. Pat. No. 5,483,965.

BACKGROUND OF THE INVENTION

1. Field of the Invention

The present invention relates to devices which are used for measuring the density of members, such as bones, and more particularly to devices which utilize ultrasonic acoustic signals to measure the physical properties and integrity of the members.

2. Description of the Prior Art

Various devices presently exist which may be used to measure the physical properties and integrity of a member such as a bone. Non-invasive density measuring devices can be used to determine cumulative internal damage caused by micro-crushing and micro-fracturing occurring in the bones of humans or animals such as race horses. Additionally, osteoporosis, or loss of bone mineralization, detection in humans and its cure or prevention are increasingly becoming areas of intense medical and biological interest. As the average age of the human population increases, a greater number of patients are developing complications due to rapid trabecular bone loss.

U.S. Pat. No. 3,847,141 to Hoop discloses a device for measuring the density of a bone structure, such as a finger bone or heel bone, to monitor the calcium content thereof. The device includes a pair of opposed spaced ultrasonic transducers which are held within a clamping device clamped on the bone being analyzed. A pulse generator is coupled to one of the transducers to generate an ultrasonic sound wave which is directed through the bone to the other transducer. An electric circuit couples the signals from the receive transducer back to the pulse generator for retriggering the pulse generator in response to those signals. The pulses therefore are produced at a frequency proportional to the transit time that the ultrasonic wave takes to travel through the bone structure, which is directly proportional to the speed of the sound through the bone. The speed of sound through a bone has been found to be proportional to the density of the bone. Thus the frequency at which the pulse generator is retriggered is proportional to the density of the bone.

Another device and method for, establishing, in vivo the strength of a bone is disclosed in U.S. Pat. Nos. 4,361,154 and 4,421,119 to Pratt, Jr. The device includes a launching transducer and a receiving transducer which are connected by a graduated vernier and which determine the speed of sound through the bone to determine its strength. The vernier is used to measure the total transit distance between the surfaces of the two transducers.

Lees (Lees, S. (1986) Sonic Properties of Mineralized Tissue, *Tissue Characterization With Ultrasound*, CRC publication 2, pp. 207-226) discusses various studies involving attenuation and speed of sound measurements in both cortical and spongy (cancellous or trabecular) bone. The results of these studies reveal a linear relationship between the wet sonic velocity and wet cortical density, and between the dry sonic velocity and the dry cortical density. The transit times of an acoustic signal through a bone member therefore are proportional to the bone density. Langton. et al. (Langton, C. M., Palmer, S. D., and Porter, S. W., (1984), The Measurement of Broad Band Ultrasonic Attenuation in Cancellous Bone, *Eng. Med.*, 13, 89-91) published the results of a study of ultrasonic attenuation versus frequency in the os calcis (heel bone) that utilized through transmission techniques. These authors suggested that attenuation differences observed in different subjects were due to changes in the mineral content of the os calcis. They also suggested that low frequency ultrasonic attenuation may be a parameter useful in the diagnosis of osteoporosis or as a predictor of possible fracture risk.

BRIEF SUMMARY OF THE INVENTION

The present invention provides an acoustic image of the human heel. The image can be used to provide greater insights into material and structural variations within the heel, to locate a consistent region of interest on a given heel, or to develop a template which can be used to improve the reproducibility of multiple measurements of a patient over several visits.

Specifically, the present invention provides an imaging ultrasonic bone densitometer with at least one ultrasonic transducer arranged to measure acoustic signals modified by different portions of the bony member. An electronic data processor receives the electrical signals corresponding to the acoustic signals and processes the signals to determine corresponding member variables related to the property of bony member at the different locations. A display communicates with the data processor to provide a measure of the bony member at the positions. The member variables may be attenuation, broad band ultrasonic attenuation (BUA), time of flight, speed of sound or a combination of these measurements.

It is thus one object of the invention to provide an ultrasonic bone densitometer providing a spatially sensitive information about bone quality.

The display may be a graphic display providing an image of the bony member, the image indicating the member variables as measured at the different locations.

It is thus another object of the invention to provide a densiometric image useful for evaluating bone quality.

The electronic data processor may operate to analyze the member variables to identify a measurement region of interest in the bone. The member variables within the region of interest may then be determined.

It is another object of the invention, therefore, to provide an imaging ultrasonic bone densitometer where the image data can be used to accurately locate a measurement region within the heel.

The densitometer may use an array of ultrasonic transducers providing a focused measurement of acoustic signals passing through a predetermined location within the bony member. The electronic data processor may scan the predetermined location through the bony member to provide a planar or volumetric image.

Thus it is another object of the invention to provide an ultrasonic bone densitometer that may produce a high resolution densiometric image. The predetermined location may be shifted electronically to obtain information for a complete image both across the transmission path of the ultrasonic signals and at different depths within the bone along the transmission path of the ultrasonic signal.

The electronic data processor may measure two locations within the bone, the first being within the trabecular region and the second at the cortical edge of the bony member.

Thus it is another object of the invention to provide a densitometer that may make two spatially separate measurements indicating different types of bone within its field of view.

The foregoing and other objects and advantages of the invention will appear from the following description. In this description, reference is made to the accompanying drawings which form a part hereof and in which there is shown by way of illustration, a preferred embodiment of the invention. Such embodiment does not necessarily represent the full scope of the invention, however, and reference must be made therefore to the claims for interpreting the scope of the invention.

BRIEF DESCRIPTION OF THE SEVERAL VIEWS OF THE DRAWINGS

FIG. 15 is an exploded view of the underside of the foot basin of FIG. 10 showing a c-clamp for holding the opposed ultrasonic transducers in precise alignment and separation;

FIG. 16 is a perspective detailed view of the shank of the c-clamp of FIG. 15 showing a lever for moving the separation of the transducers between an open and precisely separated closed position;

FIG. 17 is a cross-section of a human heel and ultrasonic transducers of the basin of FIG. 10 showing flexible liquid filled bladders surrounding the transducers and providing a coupling path between the transducers and the heel;

FIG. 20 is an exploded view of the elements of an ultrasonic detector array showing a driving mechanism for improving the resolution of the acquired data and the location of a piezoelectric film detector array above a spatially offset connector;

FIG. 21 is a detailed perspective fragmentary view of the piezoelectric film detector with electrodes on its surface as communicating with connector terminals via acoustically transparent conductors;

FIG. 22 is a detailed fragmentary view of the piezoelectric film showing a method of assembling the acoustically transparent conductors;

DETAILED DESCRIPTION OF THE INVENTION

Caliper Embodiment

Figure 1:
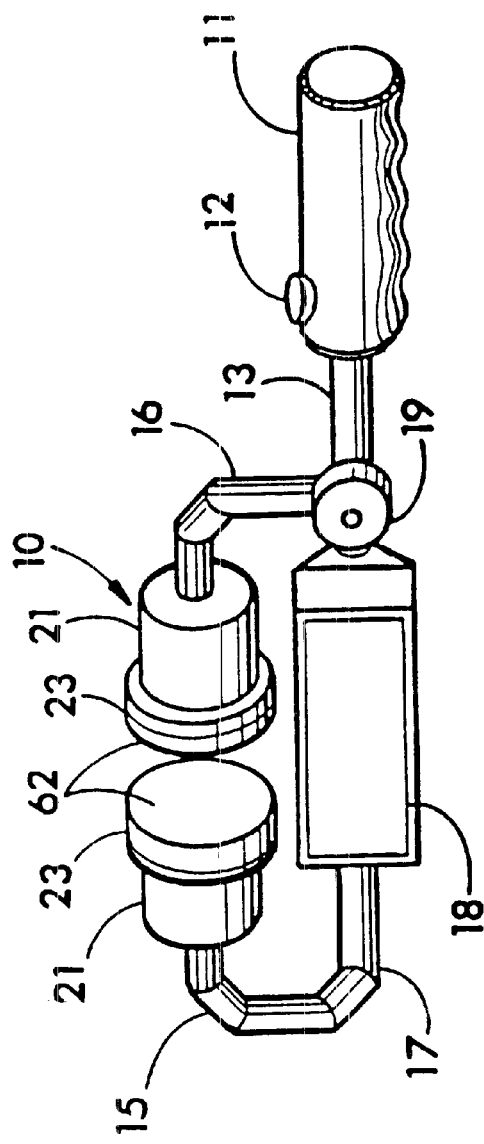
FIG. 1 is a perspective view of the ultrasound densitometer device constructed in accordance with the present invention.

Referring more particularly to the drawings, wherein like numbers refer to like parts, FIG. 1 shows a portable ultrasound densitometer 10 for measuring the physical properties and integrity of a member, such as a bone, in vivo. The densitometer 10 as shown in FIG. 1 includes a handle 11 with actuator button 12. Extending linearly from the handle 11 is a connection rod 13. The densitometer 10 also includes a fixed arm 15 and an adjustable arm 16. The fixed arm 15 preferably is formed continuously with the connection rod 13, and therefore is connected to an end 17 of the connection rod 13. The adjustable arm 16 is slidably mounted on the connection rod 13 between the handle 11 and a digital display 18 mounted on the rod 13. The knob 19 may be turned so as to be locked or unlocked to allow the adjustable arm 16 to be slid along the connection rod 13 so that the distance between the arms 15 and 16 may be adjusted.

Figure 3:
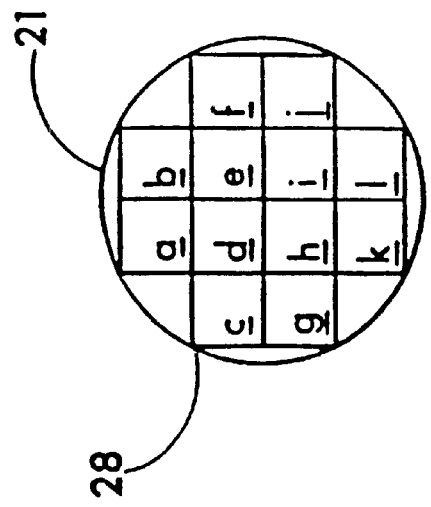
FIG. 3 is a front view of a transducer face from which acoustic signals are transmitted or by which acoustic signals are received, the face of the other transducer being the mirror image thereof.
Figure 2:
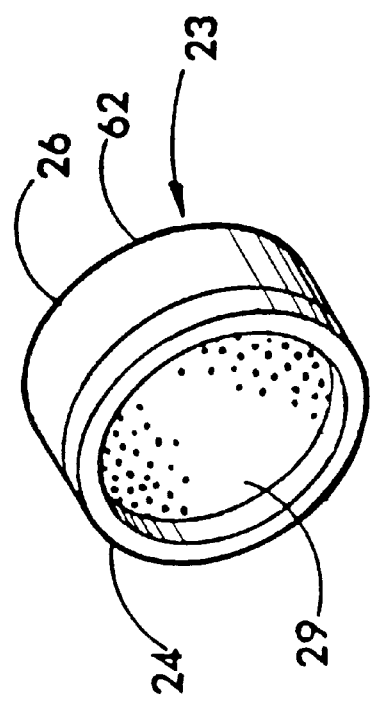
FIG. 2 is a perspective view of an acoustic coupler, two of which are shown in FIG. 1.

Connected at the end of the fixed arm 15 is a first (left) transducer 21 and at the end of the adjustable arm 16 is a second (right) transducer 21. As shown in FIGS. 1 and 2, each of the transducers 21 has mounted on it a respective compliant acoustic coupler 23 to acoustically couple the transducer to the object being tested. The acoustic coupler 23 includes a plastic ring 24 and attached pad 26 formed of urethane or other compliant material. FIG. 3 shows a face 28 of the first (left) transducer 21 which is normally hidden behind the compliant pad 26 of the acoustic coupler 23. The transducer face 28 normally abuts against the inner surface 29 of the pad 26 shown in FIG. 2. The transducer face 28 shown in FIG. 3 includes an array of twelve transducer elements labeled a-l. The second (right) transducer 21 includes a face 28 which is the mirror image of that shown in FIG. 3.

Figure 4:
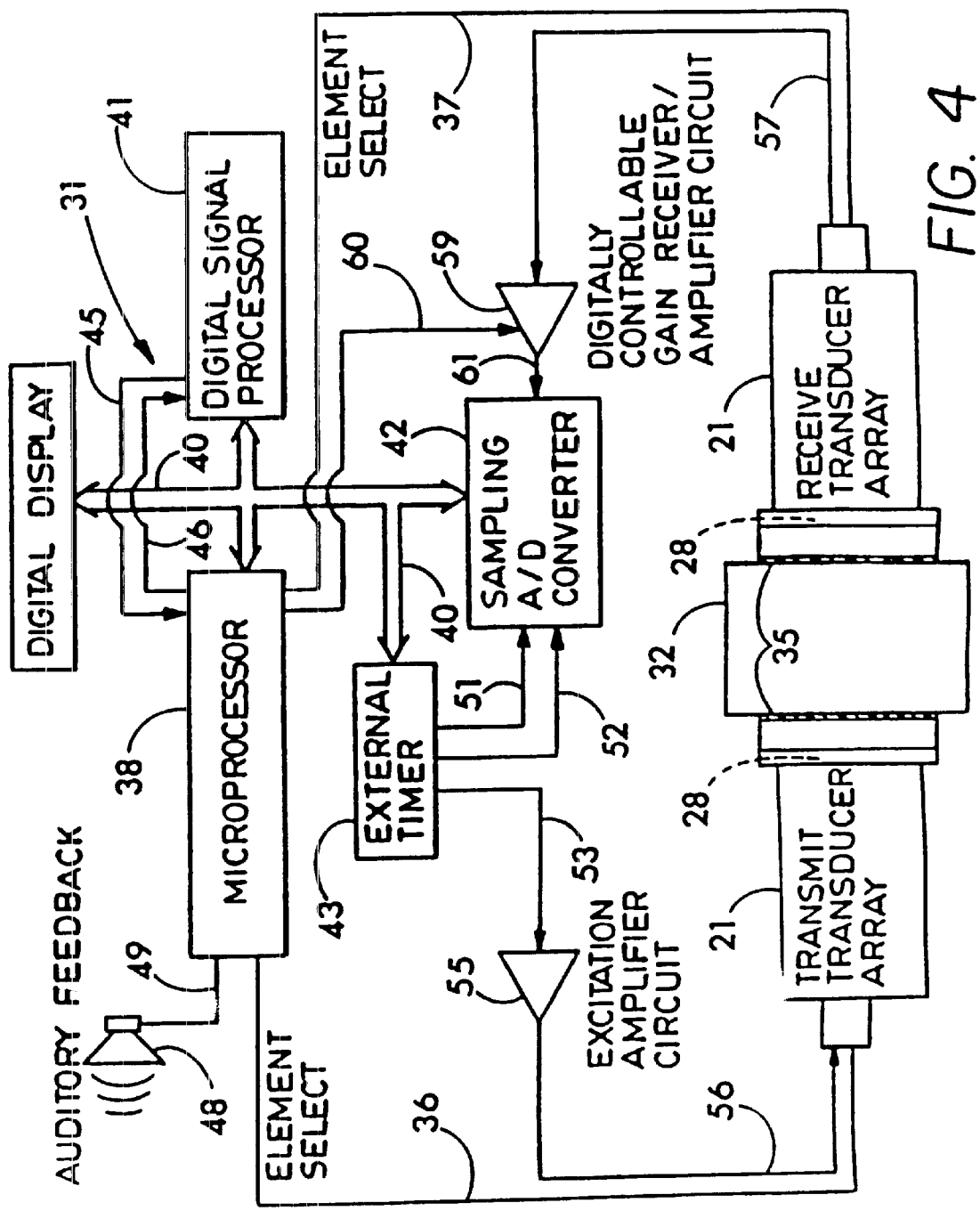
FIG. 4 is a schematic block diagram view of the circuitry of the ultrasound densitometer device constructed in accordance with the present invention.

FIG. 4 generally shows in schematic fashion the electronic circuitry 31 of the densitometer 10, which is physically contained in the housing of the digital display 18. An object 32 is placed between the two transducers 21 so that acoustic signals may be transmitted through the object. This object 32 represents a member, such as a bone, or some material with known acoustic properties such as distilled water or a neoprene reference block. As shown in the embodiment illustrated in FIG. 4, the leftmost transducer 21 is a transmit transducer and the rightmost transducer 21 a receive transducer. In fact though, either or both of the transducers 21 may be a transmit and/or receive transducer. The transmit and receive transducers 21 of the circuit of FIG. 4 are connected by element select signals 36 and 37 to a microprocessor 38. The microprocessor 38 is programmed to determine which one of the respective pairs of transducer elements a through I are to be transmitting and receiving at any one time. This selection is accomplished by the element select signal lines 36 and 37, which may be either multiple signal lines or a serial data line to transmit the needed selection data to the transducers 21. The microprocessor 38 is also connected by a data and address bus 40 to the digital display 18, a digital signal processor 41, a sampling analog to digital converter 42, and a set of external timers 43. The microprocessor 38 has "on board" electrically programmable non-volatile random access memory (NVRAM) and, perhaps as well, conventional RAM memory, and controls the operations of the densitometer 10. The digital signal processor 41 has "on board" read-only memory (ROM) and performs many of the mathematical functions carried out by the densitometer 10 under the control of the microprocessor 38. The digital signal processor 41 specifically includes the capability to perform discrete Fourier transforms, as is commercially available in integrated circuit form presently, so as to be able to convert received waveform signals from the time domain to the frequency domain. The microprocessor 38 and digital signal processor 41 are interconnected also by the control signals 45 and 46 so that the microprocessor 38 can maintain control over the operations of the digital signal processor 41 and receive status information back. Together the microprocessor 38 and the digital signal processor 41 control the electrical circuit 31 so that the densitometer 10 can carry out its operations, which will be discussed below. An auditory feedback mechanism 48, such as an audio speaker, can be connected to the microprocessor 38 through an output signal 49.

The external timer 43 provides a series of clock signals 51 and 52 to the A/D converter 42 to provide time information to the A/D converter 42 so that it will sample at timed intervals electrical signals which it receives ultimately from the transmit transducer, in accordance with the program in the microprocessor 38 and the digital signal processor 41. The external timer 43 also creates a clock signal 53 connected to an excitation amplifier 55 with digitally controllable gain. Timed pulses are generated by the timer 43 and sent through the signal line 53 to the amplifier 55 to be amplified and directed to the transmit transducer 21 through the signal line 56. The transmit transducer 21 converts the amplified pulse into an acoustic signal which is transmitted through the object or material 32 to be received by the receive transducer 21 which converts the acoustic signal back to an electrical signal. The electrical signal is directed through output signal 57 to a receiver amplifier 59 which amplifies the electrical signal.

The excitation amplifier circuit 55 is preferably a digitally controllable circuit designed to create a pulsed output. The amplification of the pulse can be digitally controlled in steps from one to ninety-nine. In this way, the pulse can be repetitively increased in amplitude under digital control until a received pulse of appropriate amplitude is received at the receiver/amplifier circuit 59, where the gain is also digitally adjustable.

Connected to the receiver amplifier circuit 59 and integral therewith is a digitally controllable automatic gain control circuit which optimizes the sensitivity of the receive transducer 21 and the amplifier circuit 59 to received acoustic signals. The microprocessor 38 is connected to the amplifier circuit and automatic gain control 59 through signal line 60 to regulate the amplification of the amplifier circuit and gain control 59. The amplified electric signals are directed through lead 61 to the A/D converter 42 which samples those signals at timed intervals. The A/D converter 42 therefore in effect samples the received acoustic signals. As a series of substantially identical acoustic signals are received by the receive transducer 21, the A/D converter 42 progressively samples an incremental portion of each successive signal waveform. The microprocessor 38 is programmed so that those portions are combined to form a digital composite waveform which is nearly identical to a single waveform. This digitized waveform may be displayed on the digital display 18, or processed for numerical analysis by the digital signal processor 41.

The densitometer constructed in accordance with FIGS. 1–4 can be operated in one or more of several distinct methods to measure the physical properties of the member, such as integrity or density. The different methods, as described in further detail below, depend both on the software programming the operation of the microprocessor 34 as well as the instructions given to the clinician as to how to use the densitometer. The different methods of use may all be programmed into a single unit, in which case a user-selectable switch may be provided to select the mode of operation, or a given densitometer could be constructed to be dedicated to a single mode of use. In any event, for the method of use of the densitometer to measure the physical properties of a member to be fully understood, it is first necessary to understand the internal operation of the densitometer itself.

In any of its methods of use, the densitometer is intended to be placed at some point in the process on the member whose properties are being measured. This is done by placing the transducers 21 on the opposite sides of the member. To accomplish this, the knob 19 is loosened to allow the adjustable arm 16 to be moved so that the transducers 21 can be placed on opposite sides of the member, such as the heel of a human patient. The outside surfaces of the pads 26 can be placed against the heel of the subject with an ultrasound gel 35 or other coupling material placed between the pads 26 and subject 32 to allow for improved transmission of the acoustic signals between the member 32 and transducers 21. Once the transducers 21 are properly placed on the member, the knob 19 may be tightened to hold the adjustable arm 16 in place, with the transducers 21 in spaced relation to each other with the member 32 therebetween. The actuator button 12 may then be pressed so that acoustic signals will be transmitted through the member 32 to be received by the receive transducer 21. The electronic circuit of FIG. 4 receives the electrical signals from the receive transducer 21, and samples and processes these signals to obtain information on the physical properties and integrity of the member 32 in vivo. The microprocessor 38 is programmed to indicate on the digital display 18 when this information gathering process is complete. Alternatively, the information may be displayed on the digital display 18 when the information gathering process is completed. For example, the transit time of the acoustic signals through the member 32 could simply be displayed on the digital display 18.

Figure 5:
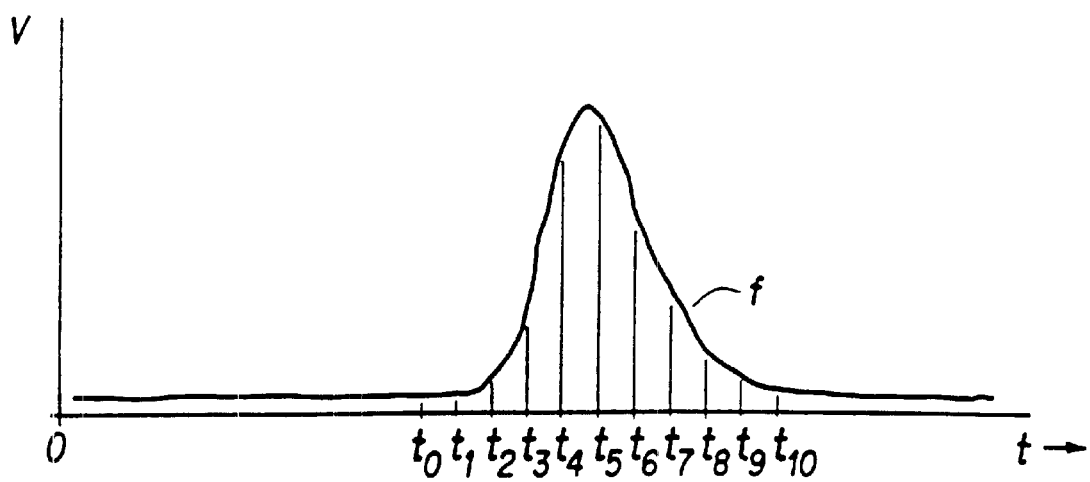
FIG. 5 illustrates the method of sampling a received waveform used by the circuit of FIG. 4.

Considering in detail the operation of the circuitry of FIG. 4, the general concept is that the circuitry is designed to create an ultrasonic pulse which travels from transmit transducer 21 through the subject 32 and is then received by the receive transducer 21. The circuitry is designed to both determine the transit time of the pulse through the member 32, to ascertain the attenuation of the pulse through the member 32, and to be able to reconstruct a digital representation of the waveform of the pulse after it has passed through the member 32, so that it may be analyzed to determine the attenuation at selected frequencies. To accomplish all of these objectives, the circuitry of FIG. 4 operates under the control of the microprocessor 38. The microprocessor 38 selectively selects, through the element select signal lines 36, a corresponding pair or a group of the elements a through l on the face of each of the transducers 21. The corresponding elements on each transducer are selected simultaneously while the remaining elements on the face of each transducer are inactive. With a given element, say for example element a selected, the microprocessor then causes the external timer 43 to emit a pulse on signal line 53 to the excitation amplifier circuit 55. The output of the excitation amplifier 55 travels along signal line 56 to element a of the transmit transducer 21, which thereupon emits the ultrasonic pulse. The corresponding element a on the receive transducer 21 receives the pulse and presents its output on the signal line 57 to the amplifier circuit 59. What is desired as an output of the A/D converter 42 is a digital representation of the analog waveform which is the output of the single transducer element which has been selected. Unfortunately, "real time" sampling A/D converters which can operate rapidly enough to sample a waveform at ultrasonic frequencies are relatively expensive. Therefore it is preferred that the A/D converter 42 be an "equivalent time" sampling A/D converter. By "equivalent time" sampling, it is meant that the A/D converter 42 samples the output of the transducer during a narrow time period after any given ultrasonic pulse. The general concept is illustrated in FIG. 5. The typical waveform of a single pulse received by the receive transducer 21 and imposed on the signal line 57 is indicated by a function "f". The same pulse is repetitively received as an excitation pulse and is repetitively launched. The received pulse is sampled at a sequence of time periods labeled $t_0$–$t_{10}$. In other words, rather than trying to do a real-time analog to digital conversion of the signal f, the signal is sampled during individual fixed time periods $t_0$–$t_{10}$ after the transmit pulse is imposed, the analog value during each time period is converted to a digital function, and that data is stored. Thus the total analog waveform response can be recreated from the individual digital values created during each time period t, with the overall fidelity of the recreation of the waveform dependent on the number of time periods t which are sampled. The sampling is not accomplished during a single real time pulse from the receive transducer 21. Instead, a series of pulses are emitted from the transmit transducer 21. The external timer is constructed to provide signals to the sampling A/D converter 42 along signal lines 51 and 52 such that the analog value sampled at time period to when the first pulse is applied to a given transducer element, then at time $t_1$ during the second pulse, time $t_2$ during the third pulse, etc. until all the time periods are sampled. Only after the complete waveform has been sampled for each element is the next element, i.e. element b, selected. The output from the A/D converter 42 is provided both to the microprocessor 38 and to the signal processor 41. Thus the digital output values representing the complex waveform f of FIG. 5 can be processed by the signal processor 41 after they are compiled for each transducer element. The waveform can then be analyzed for time delay or attenuation for any given frequency component with respect to the characteristic of the transmitted ultrasonic pulse. The process is then repeated for the other elements until all elements have been utilized to transmit a series of pulses sufficient to create digital data representing the waveform which was received at the receive transducer array 21. It is this data which may then be utilized in a variety of methods for determining the physical properties of the member. Depending on the manner in which the densitometer is being utilized and the data being sought, the appropriate output can be provided from either the microprocessor 38 or the signal processor 41 through the digital display 18.

Because the ultrasonic pulsing and sampling can be performed so rapidly, at least in human terms, the process of creating a sampled ultrasonic received pulse can optionally be repeated several times to reduce noise by signal averaging. If this option is to be implemented, the process of repetitively launching ultrasonic pulses and sampling the received waveform as illustrated in FIG. 5 is repeated one or more times for each element in the array before proceeding to the next element. Then the sampled waveforms thus produced can be digitally averaged to produce a composite waveform that will have a lesser random noise component than any single sampled waveform. The number of repetitions necessary to sufficiently reduce noise can be determined by testing in a fashion known to one skilled in the art.

Having thus reviewed the internal operation of the densitometer of FIGS. 1–4, it is now possible to understand the methods of use of the densitometer to measure the physical properties of the member. The first method of use involves measuring transit time of an ultrasonic pulse through a subject and comparing that time to the time an ultrasonic pulse requires to travel an equal distance in a substance of known acoustic properties such as water. To use the densitometer in this procedure, the adjustable arm 16 is adjusted until the member of the subject, such as the heel, is clamped between the transducers 21. Then the knob 19 is tightened to fix the adjustable arm in place. The actuator button 12 is then pressed to initiate a pulse and measurement. Next the densitometer is removed from the subject while keeping the knob 19 tight so that the distance between the transducers 21 remains the same. The device 10 is then placed about or immersed in a standard material 32 with known acoustic properties, such as by immersion in a bath of distilled water. The actuator button 12 is pressed again so that acoustic signals are transmitted from the-transmit transducer 21 through the material 32 to the receive transducer 21. While it is advantageous to utilize the whole array of elements a through 1 for the measurement of the member, it may only be necessary to use a single pair of elements for the measurement through the standard assuming only that the standard is homogeneous, unlike the member. The signal profiles received by the two measurements are then analyzed by the microprocessor 38 and the signal processor 41. This analysis can be directed both to the comparative time of transit of the pulse through the subject as compared to the standard and to the characteristics of the waveform in frequency response and attenuation through the subject as compared to the standard.

Thus in this method the densitometer may determine the physical properties and integrity of the member 32 by both or either of two forms of analysis. The densitometer may compare the transit time of the acoustic signals through the member with the transmit time of the acoustic signals through the material of known acoustic properties, and/or the device 10 may compare the attenuation as a function of frequency of the broadband acoustic signals through the member 32 with the attenuation of corresponding specific frequency components of the acoustic signals through the material of known acoustic properties. The "attenuation" of an acoustic signal through a substance is the diminution of the ultrasonic waveform from the propagation through either the subject or the standard. The theory and experiments using both of these methods are presented and discussed in Rossman, P. J., Measurements of Ultrasonic Velocity and Attenuation In The Human Os Calcis and Their Relationships to Photon Absorptiometry Bone Mineral Measurements (1987) (a thesis submitted in partial fulfillment of the requirements for the degree of Master of Science at the University of Wisconsin-Madison). Tests have indicated that there exists a linear relationship between ultrasonic attenuation (measured in decibels) (dB)) at specific frequencies, and those frequencies. The slope (dB/MHz) of the linear relationship, referred to as the broadband ultrasonic attenuation, is dependent upon the physical properties and integrity of the substance being tested. With a bone, the slope of the linear relationship would be dependent upon the bone mineral density. Thus broadband ultrasonic attenuation through a bone is a parameter directly related to the quality of the cancellous bone matrix.

The microprocessor 38 may therefore be programmed so that the device determines the physical properties and integrity of the member by comparing either relative transit times and/or relative broadband ultrasonic attenuation through the member and a material of known acoustic properties. When comparing the transit times, the microprocessor 38 may be programmed most simply so that the electronics, having received the acoustic signals after they have been transmitted through the member, determines the "member" transit time of those acoustic signals through the member, and after the acoustic signals have been transmitted through the material of known acoustic properties, determines the "material" transit time of the acoustic signals through the material. These time periods may be measured most simply by counting the number of clock pulses of known frequency emitted by the timer 43 between the time of launching the pulse and the sensing of the received pulse at the A/D converter 42. The microprocessor 38 then makes a mathematical "time" comparison of the member transit time to the material transit time and then relates that mathematical time comparison to the physical properties and integrity of the member. The mathematical time comparison may be made by either determining a difference between the member transit time and the material transit time, or by determining a ratio between the member transit time and the material transit time.

As a second method of using the densitometer, it may also determine the physical properties and integrity of the member 32 by determining and comparing the attenuation of the broadband frequency components of the acoustic signals through the member without reference to a material having known acoustic properties. Using this method, the comparison of velocity to a standard is not necessary and absolute transit time of the pulse need not be calculated since it is attenuation that is measured. In such a mode, it is preferable that the transmit transducer 21 transmits an acoustic signal which has a broad range of frequency components, such as a simple ultrasonic pulse. In any case, the acoustic signal should have at least one specific frequency component.

In this attenuation comparison mode, the microprocessor 38 is programmed so that after the receive transducer 21 receives the acoustic signals transmitted through the bone member 32, it determines the absolute attenuation through the member 32 of the frequency component spectrum of the acoustic signals. It is to facilitate the measurement of attenuation that the excitation amplifier circuit 55 and the receiver amplifier 59 have amplification levels which may be digitally controlled. By successively varying the gain of the amplifiers 55 and 59 on successive pulses, the circuit of FIG. 4 can determine what level of gain is necessary to place the peak of the received waveform at a proper voltage level. This gain is, of course, a function of the level of attenuation of the acoustic pulse during transit through the member 32. After the receive transducer 21 receives acoustic signals, microprocessor 38 in conjunction with the signal processor 41 determines the absolute attenuation of individual specific frequency components of the received acoustic signal transmitted through the material. The digital signal processor 41 then makes mathematical "attenuation" comparisons of the corresponding individual specific frequency components through the member. A set of mathematical attenuation comparisons between corresponding frequency components may be thereby obtained, one comparison for each frequency component compared. The manner in which the attenuation functions with respect to frequency can thus be derived. The microprocessor 38 and digital signal processor 41 then relate that function to the physical properties and integrity of the member.

Figure 7:
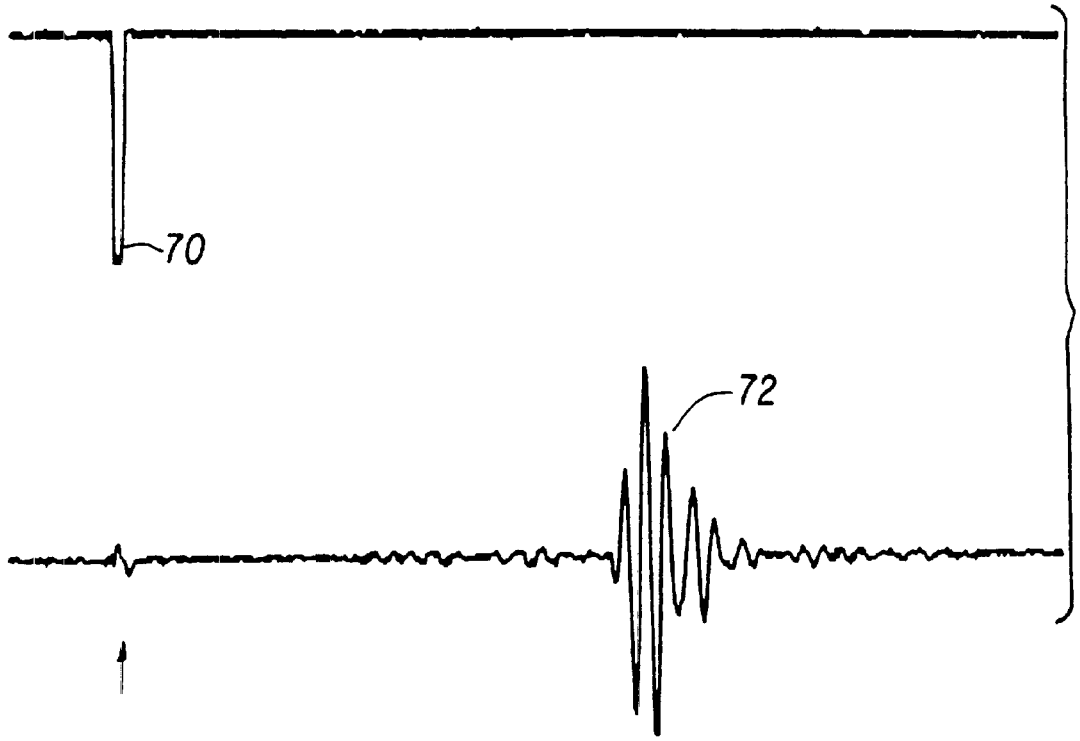
FIG. 7 is a sample of an actual ultrasonic pulse and response from an ultrasonic densitometer according to the present invention.
Figure 8:
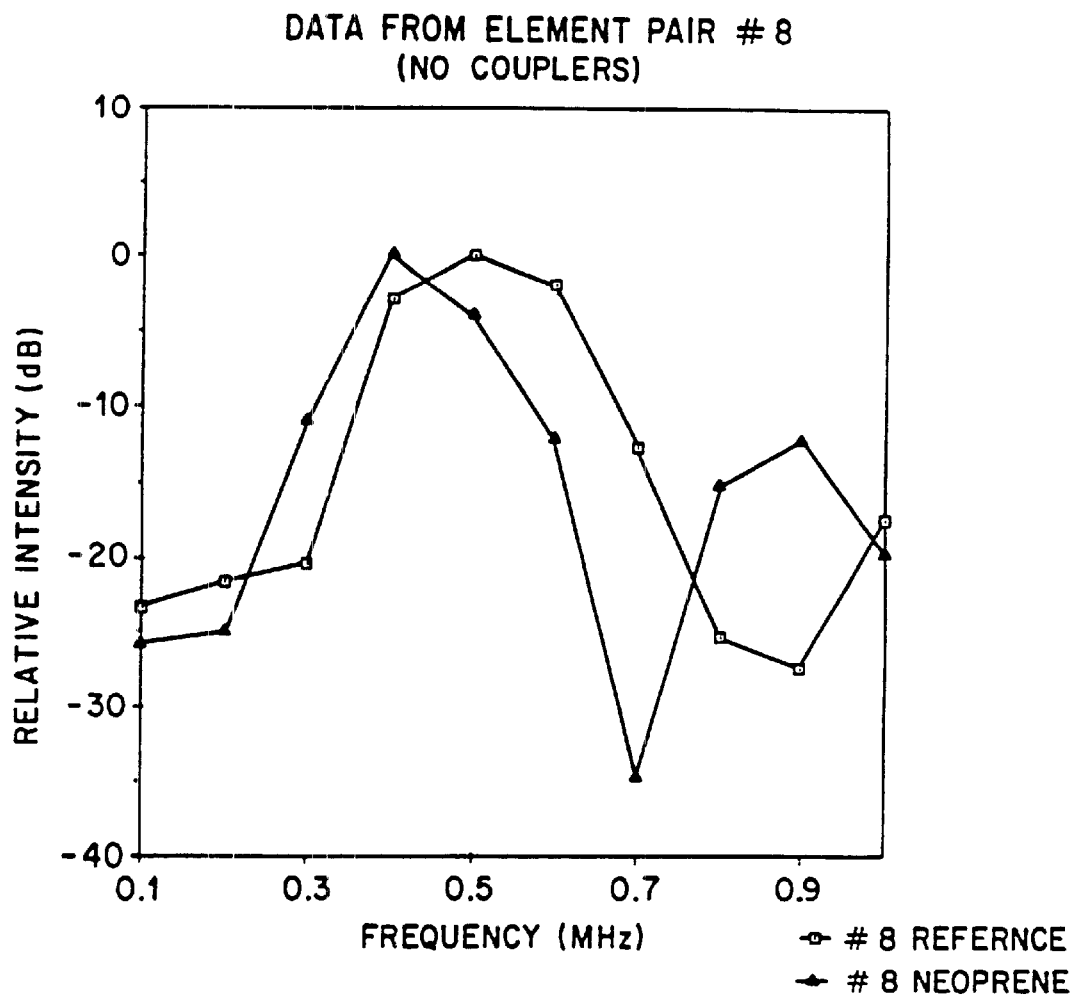
FIG. 8 is a sample plot of relative ultrasound pulse intensity over frequency range.
Figure 9:
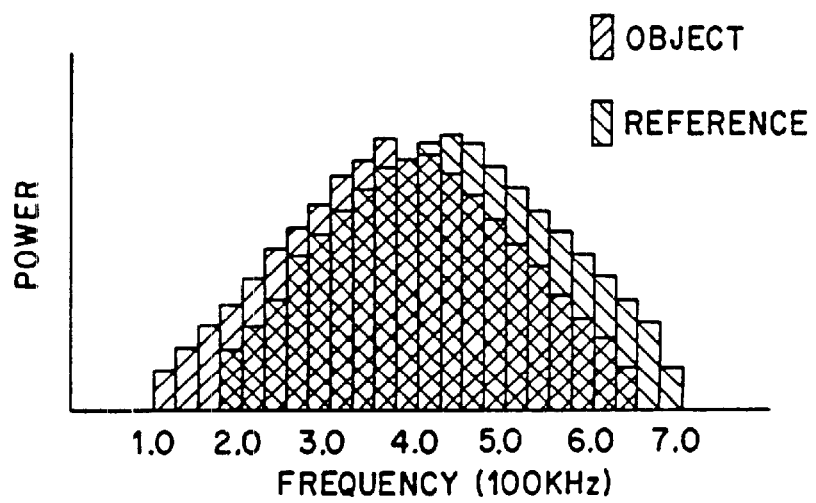
FIG. 9 is a graph in frequency domain illustrating the shift in attenuation versus frequency characteristic of a measured object as compared to a reference.

Shown in FIG. 7 is a sample broadband ultrasonic pulse and a typical received waveform. To achieve an ultrasonic signal that is very broad in the frequency domain, i.e., a broadband transmitted signal, an electronic pulse such as indicated at 70 is applied to the selected ultrasonic transducer in the transmit array 21 which then resonates with a broadband ultrasonic emission. The received signal, such as indicated at 72 in FIG. 7 in a time domain signal plot, is then processed by discrete Fourier transform analysis so that it is converted to the frequency domain. Shown in FIG. 8 is a pair of plots of sample received signals, in frequency domain plots, showing the shift in received signal intensity as a function of frequency between a reference object and a plug of neoprene placed in the instrument. FIG. 9 illustrates a similar comparison, with FIG. 8 using relative attenuation in the vertical dimension and FIG. 9 using power of the received signal using a similar reference material. Both representations illustrate the difference in relative intensities as a function of frequency illustrating how broadband ultrasonic attenuation varies from object to object. The actual value calculated, broadband ultrasonic attenuation, is calculated by first comparing the received signal against the reference signal, then performing the discrete Fourier transform to convert to frequency domain, then performing a linear regression of the difference in attenuation slope to derive broadband ultrasonic attenuation.

The mathematics of the discrete Fourier transform are such that another parameter related to bone member density may be calculated in addition to, or in substitution for, broadband attenuation (sometimes referred to as "attenuation" or "BUA" below). When the discrete Fourier transform is performed on the time-domain signal, the solution for each point includes a real member component and an imaginary member component. The values graphed in FIGS. 8 and 9 are the amplitude of the received pulse as determined from this discrete Fourier transform by taking the square root of the sum of the squares of the real component and the imaginary component. The phase angle of the change in phase of the ultrasonic pulse as it passed through the member can be calculated by taking the arctangent of the ratio of the imaginary to the real components. This phase angle value is also calculated to bone member density.

The microprocessor 38 may also be programmed so that the densitometer simultaneously performs both functions, i.e. determines both transit time and absolute attenuation of the transmitted acoustic signals, first through the member and then through the material with known acoustic properties. The densitometer may then both derive the broadband ultrasonic attenuation function and make a mathematical time comparison of the member transit time to the material transit time. The microprocessor 38 and digital signal processor 41 then relate both the time comparison along with the attenuation function to the physical properties and integrity, or density of the member 32.

In yet another possible mode of operation, the microprocessor 38 may be programmed so that the densitometer 10 operates in a mode whereby the need for calculating either the relative transit time or the attenuation of the acoustic signals through a material of known acoustic properties is eliminated. In order to operate in such a mode, the microprocessor 38 would include a database of normal absolute transit times which are based upon such factors as the age, height, weight, race or the sex of the individual being tested as well as the distance between the transducers or the thickness or size of the member. This database of normal transit times can be stored in the non-volatile memory or could be stored in other media. When testing an individual in this mode, the relevant factors for the individual are placed into the microprocessor 38 to select the pertinent normal transit time based on those factors. The transducers 21 are placed on the bone member being tested as described above. When the actuator button 12 is pressed, the acoustic signals are transmitted through the member 32. The receive transducer 21 receives those signals after they have been transmitted through the member, and the electronics 31 then determine the "member" transit time of the acoustic signals through the member. The microprocessor 38 and digital signal processor 41 then make a mathematical comparison of the measured member transit time to the selected database normal transit time, and relate the mathematical time comparison to the physical properties and integrity, or density of the member, which is displayed.

As an alternative output of the densitometer of the present invention, the digital display 18 could also include a display corresponding to the pattern of the array of elements on the face of the transducer 21 as seen in FIG. 3. This display could then display, for each element a through 1, a gray scale image proportional to the parameter, i.e. transit time or attenuation, being measured. This image may provide a visual indication to an experienced clinician as to the physical properties of the member present in the patient.

Figure 6:
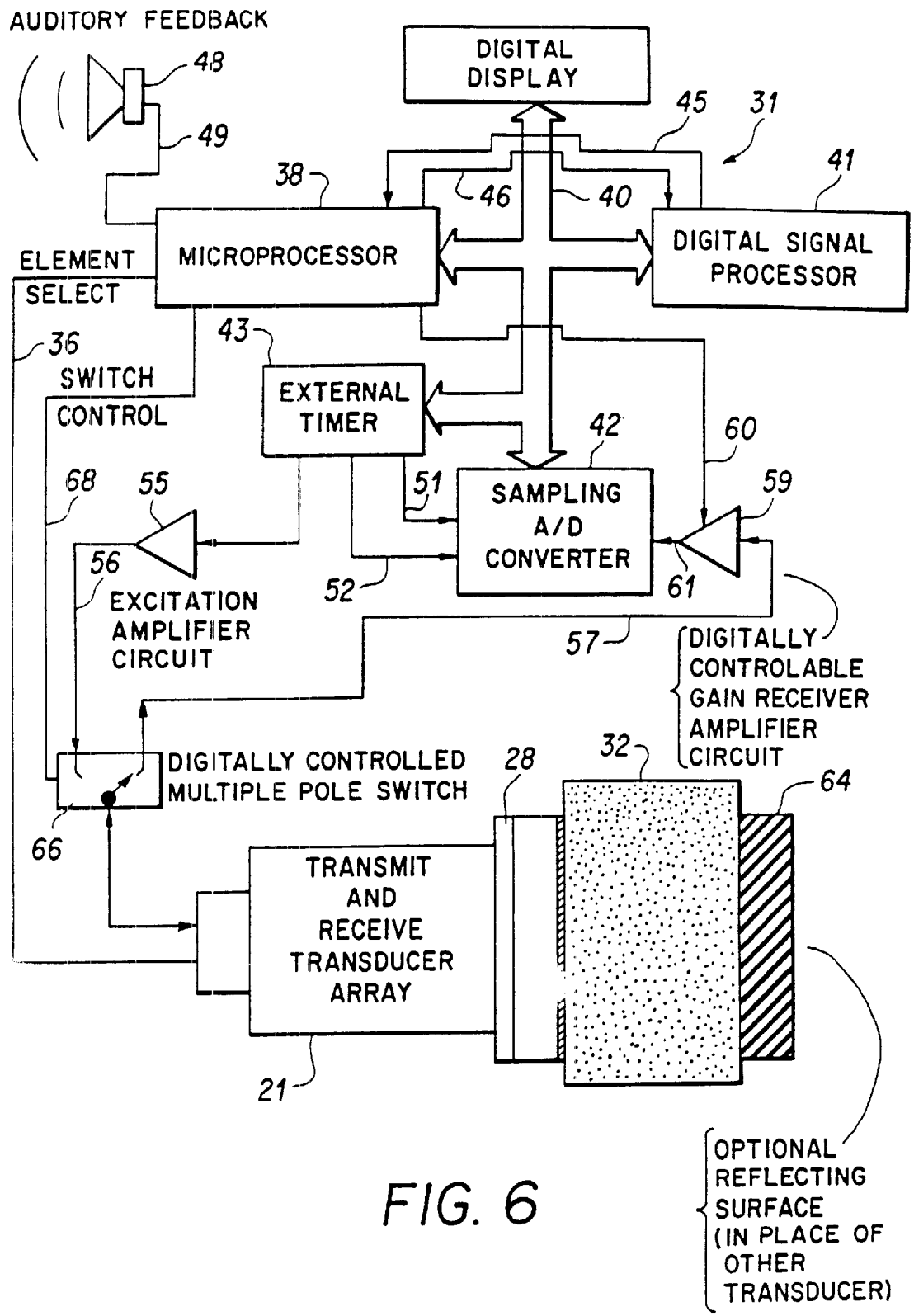
FIG. 6 is a schematic block diagram view of the circuitry of an alternative embodiment of an ultrasound densitometer constructed in accordance with the present invention.

Shown in FIG. 6 is a circuit schematic for an alternative embodiment of an ultrasonic densitometer constructed in accordance with the present invention. In the circuit of FIG. 6, parts having similar structure and function to their corresponding parts in FIG. 4 are indicated with similar reference numerals.

The embodiment of FIG. 6 is intended to function with only a single transducer array 21 which functions both as the transmit and the receive transducer array. An optional reflecting surface 64 may be placed on the opposite side of the member 32 from the transducer array 21. A digitally controlled multiple pole switch 66, preferably an electronic switch rather than a mechanical one, connects the input to and output from the elements of the transducer array 21 selectively either to the excitation amplifier 55 or to the controllable gain receiver/amplifier circuit 59. The switch 66 is connected by a switch control line 68 to an output of the microprocessor 38.

In the operation of the circuit of FIG. 6, it functions in most respects like the circuit of FIG. 4, so only the differences need be discussed. During the launching of an ultrasonic pulse, the microprocessor 38 causes a signal to appear on the switch control line 68 to cause the switch 66 to connect the output of the excitation amplifier 55 to the selected element in the transducer array 21. Following completion of the launching of the pulse, the microprocessor 38 changes the signal on the switch control line 68 to operate the switch 66 to connect the selected element or elements as an input to the amplifier 59. Meanwhile, the pulse propagates through the member 32. As the pulse transits through the member, reflective pulses will be generated as the pulse crosses interfaces of differing materials in the member and, in particular, as the pulse exits the member into the air at the opposite side of the member. If the transition from the member to air does not produce a sufficient reflective pulse, the reflecting surface 64 can be placed against the opposite side of the member to provide an enhanced reflected pulse.

The embodiment of FIG. 6 can thus be used to analyze the physical properties and integrity of a member using only one transducer 21. All of the methods described above for such measurements may be used equally effectively with this version of the device. The transit time of the pulse through the member can be measured simply by measuring the time period until receipt of the reflected pulse, and then simply dividing by two. This time period can be compared to the transit time, over a similar distance, through a standard medium such as water. The time period for receipt of the reflected pulse could also be simply compared to standard values for age, sex, etc. Attenuation measurements to detect differential frequency measurement can be directly made on the reflected pulse. If no reflecting surface 64 is used, and it is desired to determine absolute transit time, the thickness of the member or sample can be measured.

The use of the multi-element ultrasonic transducer array for the transducers 21, as illustrated in FIG. 3, enables another advantageous feature of the instrument of FIGS. 1–9. In using prior art densitometers, it was often necessary to precisely position the instrument relative to the body member of the patient being measured to have useful results. The difficulty arises because of heterogeneities in the bone mass and structure of actual body members. A measurement taken at one location of density may be significantly different from a measurement taken close by. Therefore prior art instruments fixed the body member precisely so that the measurement could be taken at the precise location each time.

The use of the ultrasonic transducer array obviates the need for this precise positioning. Using the instrument of FIGS. 1–9, the instrument performs a pulse and response, performs the discrete Fourier transform, and generates a value for broadband ultrasonic attenuation for each pair of transducer elements a through l. Then the microprocessor 38 analyzes the resulting array of bone ultrasonic density measurements to reproducibly identify the same region of interest each time. In other words, since the physical array of transducers is large enough to reliably cover at least the one common region of interest each time, the measurement is localized at the same locus each time by electrically selecting the proper location for the measurement from among the locations measured by the array. The instrument of FIGS. 1–9 is conveniently used by measuring the density of the os calcis as measured through the heel of a human patient. When used in this location, it has been found that a region of interest in the os calcis can be located reliably and repeatedly based on the comparisons of broadband ultrasonic attenuation at the points in the array. The region of interest in the os calcis is identified as a local or relative minimum in broadband ultrasonic attenuation and/or velocity closely adjacent the region of highest attenuation values in the body member. Thus repetitive measurements of the broadband ultrasonic attenuation value at this same region of interest can be reproducibly taken even though the densitometer instrument 10 is only generally positioned at the same location for each successive measurement.

This technique of using a multiple element array to avoid position criticality is applicable to other techniques other than the determination of broadband ultrasonic attenuation as described here. The concept of using an array and comparing the array of results to determine measurement locus would be equally applicable to measurements taken of member-density based on speed of sound transit time, other measurements of attenuation or on the calculation of phase angle discussed above. The use of such a multiple-element array, with automated selection of one element in the region of interest, can also be applied to other measurement techniques useful for generating parameters related to bone member density, such as measuring speed changes in the transmitted pulse such as suggested in U.S. Pat. No. 4,361,154 to Pratt, or measuring the frequency of a "sing-around" self-triggering pulse as suggested in U.S. Pat. No. 3,847,141 to Hoop. The concept which permits the position independence feature is that of an array of measurements generating an array of data points from which a region of interest is selected by a reproducible criterion or several criteria. The number of elements in the array also clearly can be varied with a larger number of elements resulting in a greater accuracy in identifying the same region of interest.

In this way, the ultrasound densitometer of the present invention provides a device capable of rapid and efficient determination of the physical properties of a member in vivo without the use of radiation. Because the densitometer is constructed to operate under the control of the microprocessor 38, it can be programmed to operate in one of several modes, as discussed above. This allows both for flexibility to clinical goals as well as efficient use of the device.

Basin Embodiment

Figure 10:
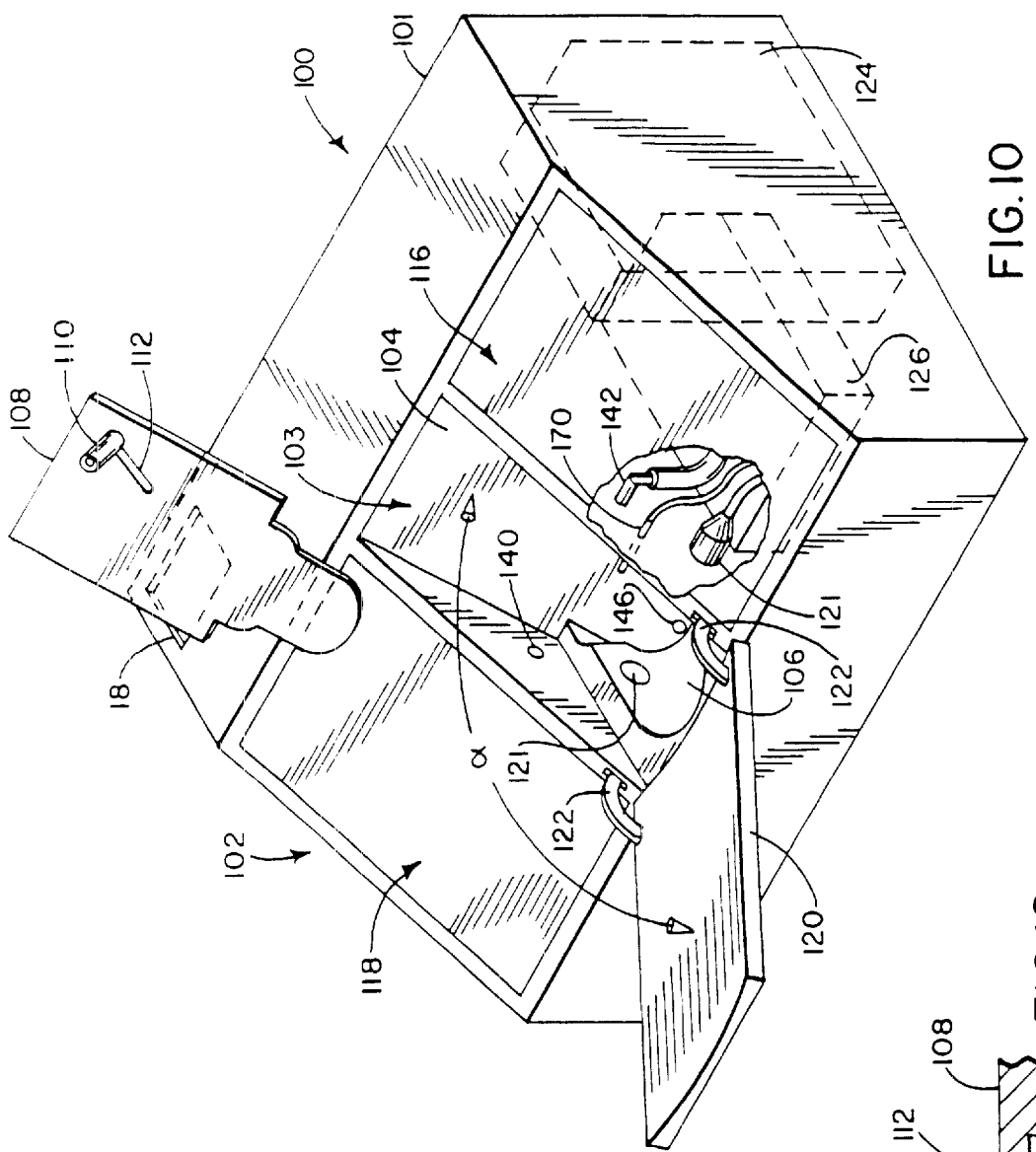
FIG. 10 is a perspective view of an alternative embodiment of the present invention showing a basin for receiving a patient's foot and having integral opposed ultrasonic transducers.

Shown in FIG. 10 is another variation on an ultrasonic densitometer constructed in accordance with the present invention. In the densitometer 100 of FIG. 10, there are two ultrasonic transducer arrays 121, which are generally similar to the ultrasonic transducer arrays 21 of the embodiment of FIG. 1, except that the transducer arrays 21 are fixed in position rather than movable.

The densitometer 100 includes a generally box-shaped mounting case 101 with sloping upper face 102 in which is formed a basin 103. The basin 103 is sized to receive a human foot and is generally trigonous along a vertical plane aligned with the length of the foot so that when the foot is placed within the basin 103, the toes of the foot are slightly elevated with respect to the heel of the foot.

The transducer arrays 121 are positioned in the case 101 so that they extend into the basin 103 to be on opposite sides of the heel of the foot placed in the basin 103. When the foot is in position within the basin 103, the sole of the foot may rest directly on a bottom 104 of the basin 103 with the heel of the foot received within a curved pocket 106 forming a back wall of the basin 103. As so positioned, the transducer arrays 121 are on either side of the os calcis. It has been demonstrated that placing the transducer approximately 4 centimeters up from the sole and 3.5 centimeters forwardly from the rearward edge of the heel places the transducers in the desired region and focused on the os calcis.

Figure 11:
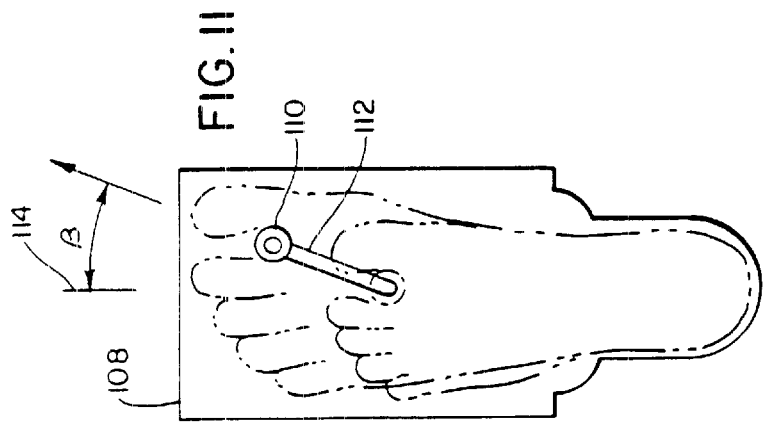
FIG. 11 is a plan view of a foot plate and toe peg used with the embodiment of FIG. 10.

The foot may, alternatively, rest on a generally planar foot plate 108 having a contour conforming to the bottom 104 and placed against the bottom 104 between the foot and the bottom 104. The foot plate 108 holds an upwardly extending toe peg 110 for use in reducing motion of the foot during the measurement process. Referring to FIG. 11, the toe peg 110 is sized to fit between the big toe and the next adjacent toe of a typical human foot and is mounted in a slot 112 so as to be adjustable generally along the length of the foot to accommodate the particular length of the foot.

The slot 112 cants inward toward a medial axis 114 of the foot, defined along the foot's length, as one moves along the slot 112 towards the portion of the foot plate 108 near the heel of the foot. This canting reflects the general relation between foot length and width and allows simple adjustment for both dimensions at once.

The toe peg 110 is sized to fit loosely between the toes of the foot without discomfort and does not completely prevent voluntary movement of the foot. Nevertheless, it has been found that the tactile feedback to the patient provided by the toe peg 110 significantly reduces foot movement during operation of the densitometer 100. Two different foot plates 108, being mirror images of each other, are used for the left and right foot.

Figure 12:
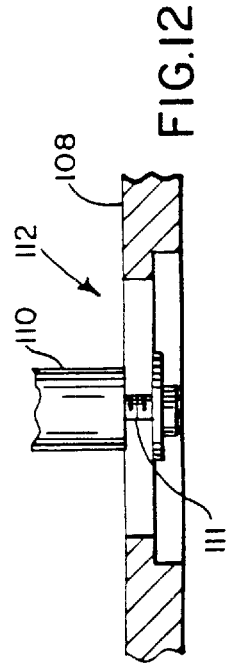
FIG. 12 is a cross-sectional detail of the foot plate of FIG. 11 showing the method of attaching the sliding toe peg of the foot plate.

Referring to FIG. 12, the toe peg 110 is held to the slot 112 by a fastener 111 having a threaded portion which engages corresponding threads in the toe peg 110. The head of the threaded fastener 111 engages the slot 112 so as to resist rotation. Thus, the toe peg 110 may be fixed at any position along the length of the slot 112 by simply turning the toe peg 110 slightly about its axis to tighten the threaded fastener 111 against the foot plate 108.

Referring again to FIG. 10, the basin 103 of the densitometer 110 is flanked, on the upper face 102 of the enclosure 101, by two foot rest areas 116 and 118 on the left and right side respectively. For examination of a patient's right foot, the patient's left foot may rest on foot rest area 118 while the patient's right foot may be placed within basin 103. Conversely, for examination of the patient's left foot, the left foot of the patient is placed within basin 103 and the patient's right foot may rest on foot rest area 116. The foot rest areas have a slope conforming to that of the upper face 102 and approximately that of bottom 104. The flanking foot rest areas 116 and 118 allow the densitometer 100 to be used in comfort by a seated patient.

When the densitometer 100 is not in use, the basin area 103 is covered with a generally planar cover 120 hinged along the lower edge of the basin 103 to move between a closed position substantially within the plane of the upper face 102 and covering the basin 103, and an open position with the plane of the cover 120 forming an angle a with the bottom 104 of the basin 103 as held by hinge stops 122. The angle a is approximately 90° and selected so as to comfortably support the calf of the patient when the patient's foot is in place within basin 103. To that end, the upper surface of the cover 120, when the cover 120 is in the open position, forms a curved trough to receive a typical calf.

The support of the patient's calf provided by the cover 120 has been found to reduce foot motion during operation of the densitometer 100.

Referring now to FIGS. 10 and 12, because the densitometer 100 employs fixed transducers 121, a coupling liquid is provided in the basin 103 to provide a low loss path for acoustic energy between the transducers 121 and the patient's foot regardless of the dimensions of the latter. The coupling liquid is preferably water plus a surfactant, the latter which has been found to improve the signal quality and consistency of the reading of the densitometer. The surfactant may be, for example, a commercially available detergent. It will be recognized, however, that other flowable, acoustically conductive media may be used to provide acoustic coupling, and hence, that the term "coupling liquid" should be considered to embrace materials having a viscosity higher than that of water such as, for example, water based slurries and thixotropic gels.

For reasons of hygiene, the exhaustion of the surfactant, and possible reduction of signal quality with the collection of impurities in the coupling liquid, it has been determined that the liquid in the basin 103 should be changed in between each use of the densitometer 103. Changing this liquid is time consuming and ordinarily would require convenient access to a sink or the like, access which is not always available. Failure to change the liquid may have no immediate visible effect, and hence changing the liquid is easy to forget or delay. For this reason, the present embodiment employs an automated liquid handling system linked to the ultrasonic measurement operation through circuitry controlled by microprocessor 38 to be described.

Figure 13:
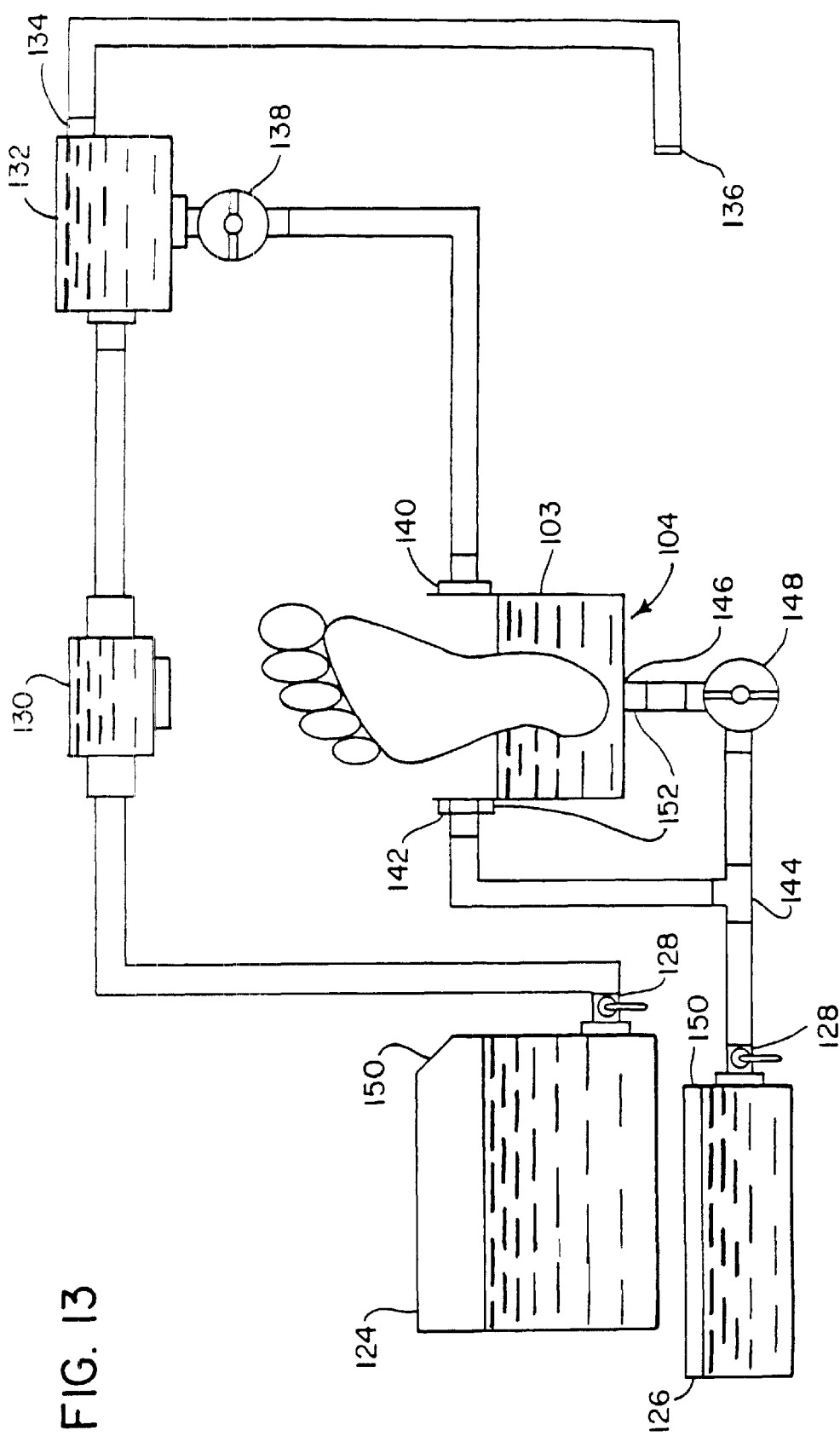
FIG. 13 is a block diagram of a system for transporting the acoustic coupling liquid used in the embodiment of FIG. 10.

Referring to FIG. 13 in the present embodiment, premixed water and surfactant for filling the basin 103 are contained in a removable polypropylene supply tank 124, whereas exhausted water and surfactant from the basin 103 are received by a similar drain tank 126. Each tank 124 and 126 contains a manual valve 128 which is opened when the tanks are installed in the densitometer 100 and closed for transporting the tanks to a remote water supply or drain. The supply tank 124 and the drain tank 126 have vents 150, at their upper edges as they are normally positioned, to allow air to be drawn into or expelled from the interior of the tanks 124 and 126 when they are in their normal position within the densitometer 100 and valves 128 are open. The tanks 124 and 126 hold sufficient water for approximately a day's use of the densitometer 100 and thus eliminate the need for convenient access to plumbing.

The valve 128 of the supply tank 124 connects the tank through flexible tubing to a pump 130 which may pump liquid from the supply tank 124 to a heating chamber 132.

Figure 14:
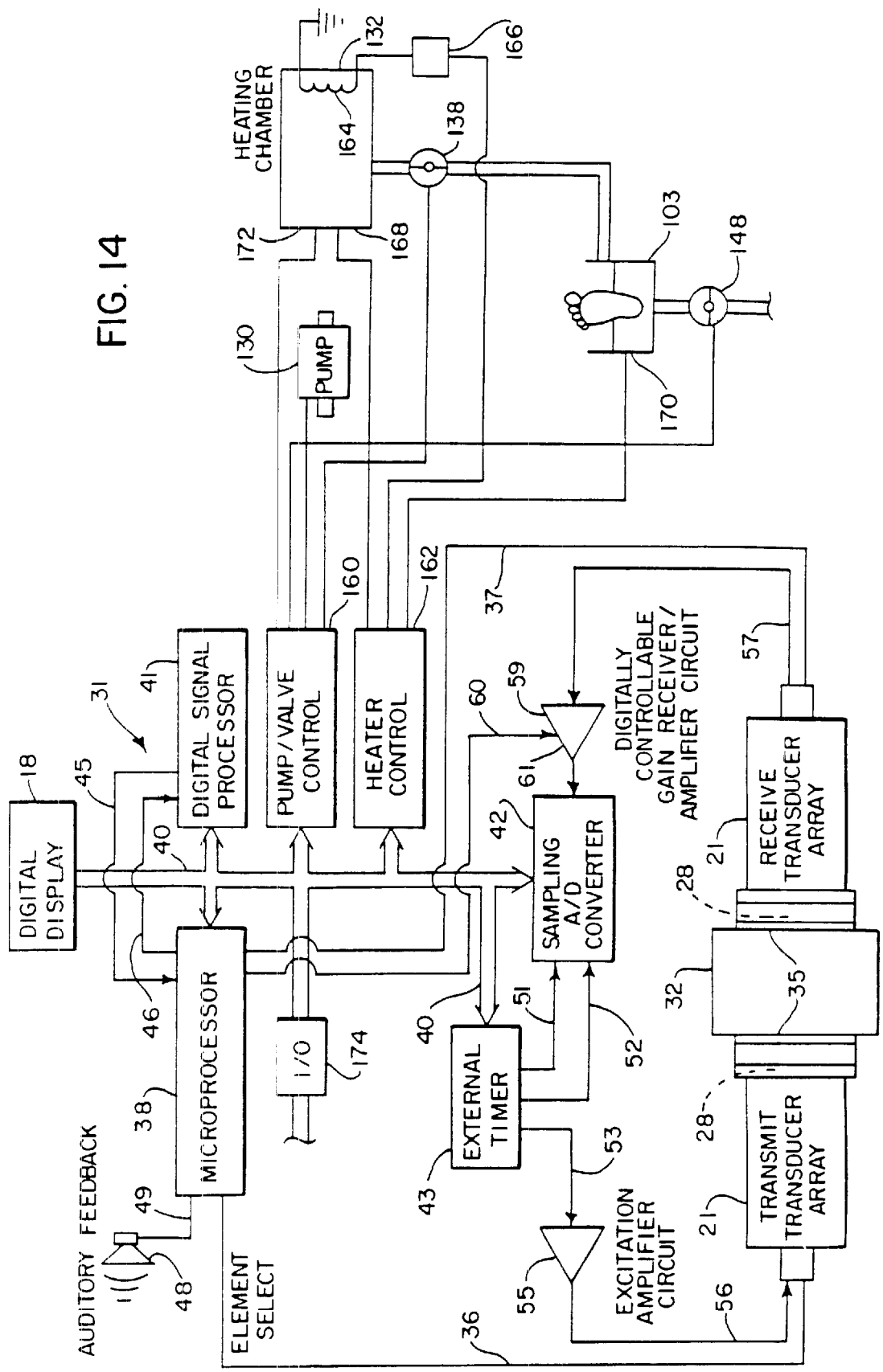
FIG. 14 is a schematic block diagram view of the circuitry of the embodiment of FIG. 10.

Referring to FIG. 14, the heating chamber 132 incorporates a resistive heating element 164 which is supplied with electrical current through a thermal protection module in thermal contact with the coupling liquid in the heating chamber 132. The thermal protection module 166 includes a thermostat and a thermal fuse, as will be described below. A thermistor 168, also in thermal communication with the liquid in the heating chamber, provides a measure of the liquid's temperature during operation of the densitometer 100. The heater chamber 132 additionally incorporates an optical level sensor 172. The level sensor 172 detects the level of liquid in the heating chamber 132 by monitoring changes in the optical properties of a prism system when the prism is immersed in liquid as opposed to being surrounded by air. The operation of the thermistor 168 and the level sensor 172 will be described further below.

Referring again to FIG. 13, the heating chamber 132 communicates through an overflow port 134 and flexible tubing to an overflow drain outlet 136. The overflow outlet 136 is positioned at the bottom of the densitometer 100 removed from its internal electronics. The overflow port 134 is positioned above the normal fill height of the heating chamber 132 as will be described in detail below.

The heating chamber 132 also communicates, through its lowermost point, with an electrically actuated fill valve 138 which provides a path, through flexible tubing, to a fill port 140 positioned in the wall of basin 103.

In the opposite wall of the basin 103 is an overflow port 142 which opens into the basin 103 at a point above the normal fill height of the basin 103 and which further communicates, through a T-connector 144, to the drain tank 126.

A drain 146, in the bottom 104 of the basin 103, provides a path to an electronically actuated drain valve 148. The drain valve 148 operates to allow liquid in the basin 103 to flow through the drain 146 to the T-connector 144 and into the drain tank 126. The overflow port 142 and drain 146 incorporate screens 152 to prevent debris from clogging the tubing or the drain valve 148 communicating with the drain tank 126.

Referring now to FIGS. 10 and 13, the supply tank 124 and the drain tank 126 are positioned within the case 101 of the densitometer 100 and located at a height with respect to the basin 103 so that liquid will drain from the basin 103 into the drain tank 126 solely under the influence of gravity and so that gravity alone is not sufficient to fill the basin 103 from supply tank 124 when fill valve 138 is open. Further, the heating chamber 132 is positioned above the basin 103 so that once the heating chamber 132 is filled with liquid by pump 130, the filling of the basin 103 from the heating chamber 132 may be done solely by the influence of gravity. Accordingly, the operation of the densitometer in filling and emptying the basin 103 is simple and extremely quiet.

In those situations where plumbing is readily accessible, either or both of the supply and drain tanks 124 and 126 may be bypassed and direct connections made to existing drains or supply lines. Specifically, the pump 130 may be replaced with a valve (not shown) connecting the heating chamber 132 to the water supply line. Conversely, the connection between the T-connector 144 and the drain tank 126 may re-routed to connect the T-connector 144 directly to a drain.

Even with the constant refreshing of the coupling liquid in the basin 103 by the liquid handling system of the present invention, the liquid contacting surfaces of the basin 103, the heating chamber 132, the valves 138 and 148, and the connecting tubing are susceptible to bacterial colonization and to encrustation by minerals. The coatings of colonization or encrustation are potentially unhygienic and unattractive. Sufficient build-up of minerals or bacteria may also adversely affect the operation of the densitometer 100 either by restricting liquid flow through the tubing, by interfering with the operation of the valves 138 or 148, or by adversely affecting the acoustical properties of the transducer array 121.

For this reason, the densitometer 100 is desirably periodically flushed with an antibacterial solution and a weak acid, the latter to remove mineral build-up. These measures are not always effective or may be forgotten, and hence, in the present invention critical water contacting surfaces are treated with a superficial antibacterial material which is also resistant to mineral encrustation. The preferred treatment is the SPI-ARGENTÔ surface treatment offered by the Spire Corporation of Bedford, Mass. which consists of an ion beam assisted deposition of silver into the treated surfaces. The resulting thin film is bactericidal, fungistatic, biocompatible, and mineral resistant. The properties of being both bactericidal and fungistatic are generally termed infection resistant.

This surface treatment is applied to the water contacting surfaces of the basin 103, the heating chamber 132 and the critical moving components of the valves 138 and 148.

Referring now to FIG. 14, the general arrangement of the electrical components of FIG. 4 is unchanged in the ultrasonic densitometer 100 of FIG. 10 except for the addition of I/O circuitry and circuitry to control the pump 130, valves 138 and 148, and heating chamber 132 of the liquid handling system. In particular, microprocessor 38 now communicates through bus 40 with an I/O module 174, a pump/valve control circuit 160 and a heater control circuit 162.

I/O module 174 provides the ability to connect a standard video display terminal or personal computer to the densitometer 100 for display of information to the user or for subsequent post processing of the data acquired by the densitometer and thus allows an alternative to microprocessor 38 and display 18 for processing and displaying the acquired ultrasound propagation data.

The pump/valve control circuit 160 provides electrical signals to the fill valve 138 and the drain valve 148 for opening or closing each valve under the control of the microprocessor 38. The pump/valve control circuit 160 also provides an electrical signal to the pump 130 to cause the pump to begin pumping water and surfactant from the supply tank 124 under the control of microprocessor 38, and receives the signal from the level sensor 172 in the heating chamber 132 to aid in the control of the pump 130 and valve 138.

The heater control circuit 162 controls the current received by the resistive heating element 164 and also receives the signal from a thermistor 168 in thermal contact with the heating chamber 132. A second thermistor 170, positioned in basin 103 to be thermal contact with the liquid in that basin 103, is also received by the heater control circuit 162.

Referring now to FIGS. 13 and 14, during operation of the densitometer 100 and prior to the first patient, the basin 103 will be empty, the supply tank 124 will be filled and contain a known volume of water and surfactant, and the drain tanks 126 will be empty. Both manual valves 128 will be open to allow flow into or out of the respective tanks 124 and 126 and the electrically actuated fill valve 138 and drain valve 148 will be closed.

Under control of microprocessor 38, the pump/valve control circuit 160 provides current to the pump 130 which pumps water and surfactant upward into heating chamber 132 until a signal is received from level sensor 172. When the heating chamber 132 is filled to the proper level as indicated by level sensor 172, the signal from level sensor 172 to pump/valve control circuit 160 causes the pump 130 to be turned off. At this time, a predetermined volume of liquid is contained in heating chamber 132 which translates to the proper volume needed to fill basin 103 for measurement.

Under command of microprocessor 38, the heater control circuit 162 provides a current through thermal protection module 166 to resistive heating element 164. The temperature of the liquid in the heating chamber 132 is monitored by thermistor 168 and heating continues until the liquid is brought to a temperature of approximately 39° C. The thermistor and a thermal fuse (not shown) of the thermal protection module 166 provide additional protection against overheating of the liquid. The thermistor opens at 50° C. and resets automatically as it cools and the thermal fuse opens at 66° C. but does not reset and must be replaced. The opening of either the thermistor or the thermal fuse interrupts current to the resistive heating element 164.

When the liquid in the heating chamber 132 is brought to the correct temperature, fill valve 138 is opened by microprocessor 38, through pump/valve control circuit 160, and liquid flows under the influence of gravity into the basin 103 at the proper temperature. The control of the temperature of the liquid serves to insure the comfort of the patient whose foot may be in the basin 103 and to decrease any temperature effects on the sound transmission of the water and surfactant.

Once the heated liquid has been transferred from the heating chamber 132 to the basin 103, the fill valve 138 is closed and the pump 130 is reactivated to refill the heating chamber 132. Thus, fresh liquid for the next measurement may be heated during the present measurement to eliminate any waiting between subsequent measurements.

With liquid in place within the basin 103, the measurement of the os calcis by the densitometer 100 may begin. In this respect, the operation of the ultrasonic densitometer of FIG. 10 is similar to that of the embodiment of FIG. 1 except that the order of pulsing and measurement can be varied. In the apparatus of FIG. 1, the measurement pulse through the member was generally performed before the reference pulse through homogenous standard, i.e. water. In the densitometer 100 of FIG. 10, since the distance between the transducers 121 is fixed, the reference pulse through the homogenous standard material, which is simply the liquid in basin 103, may be conducted before or after a measurement pulse through a live member is performed. In fact, because the temperature of the liquid in the basin 103 is held steady by the temperature control mechanism as described, the standard transmit time measurement can be made once for the instrument and thereafter only measurement pulses need be transmitted.

Preferably, the standard transit time measurement is stored as a number in the memory of microprocessor 38 during the initial calibration of the unit at the place of manufacture or during subsequent recalibrations. During the calibration of the densitometer 100, the signal from the thermistor 170 is used to produce a transit time corrected for the temperature of the liquid according to well known functional relations linking the speed of sound in water to water temperature. It is this corrected transit time that is stored in the memory associated with microprocessor 38 as a stored standard reference.

The transit time of the measurement pulses is compared to the stored standard reference transit times through the coupling liquid to give an indication of the integrity of the member just measured. Thus, one may dispense with the reference pulse entirely. Empirical tests have determined that by proper selection of a standard reference value stored in the memory of microprocessor 38 and by holding the liquid in the basin within a temperature range as provided by the heating chamber 132, no reference pulse need be launched or measured.

Using this variation, a mathematical comparison of the measured transit time, or transit velocity, must be made to the standard. Since, in the interests of accuracy, it is preferred to use both changes in transit time (velocity) and changes in attenuation to evaluate a member in vivo, the following formula has been developed to provide a numerical value indicative of the integrity and mineral density of a bone:

$$\text{bone integrity value} = A(SOS-B) + C(BUA-D) \tag{1}$$

In this formula, "SOS" indicates the speed of sound, or velocity, of the measurement ultrasonic pulse through the member, and is expressed in meters per second. The speed of sound (SOS) value is calculated from the measured transit time by dividing a standard value for the member width by the actual transit time measured. For an adult human heel, it has been found that assuming a standard human heel width of 40 mm at the point of measurement results in such sufficient and reproducible accuracy that actual measurement of the actual individual heel is not needed.

BUA is broadband ultrasonic attenuation, as described in greater detail above. The constants A, B, C, and D offset and scale the influence of the BUA measurement relative to the SOS measurement to provide a more effective predictor of bone density. These constants may be determined empirically and may be selected for the particular machine to provide numbers compatible with dual photon absorptiometry devices and to reduce bone width effects. Since this method utilizing ultrasonic measurement of the heel is quick and free from radiation, it offers a promising alternative for evaluation of bone integrity.

The densitometer 100 may be used with or without an array of ultrasonic ransducers in the transducers 121. In its simplest form the mechanical alignment of the heel in the device can be provided by the shape and size of the basin 103. While the use of an array, and region-of-interest scanning as described above, is most helpful in ensuring a reproducible and accurate measurement, mechanical placement may be acceptable for clinical utility, in which case only single transducer elements are required.

Upon completion of the measurement, the drain valve 148 is opened by microprocessor 38 through pump/valve control circuitry 160, and the liquid in the basin 103 is drained through "T" 144 to the drain tank 126. At the beginning of the next measurement, the drain valve 148 is closed and liquid is again transferred from the heating chamber 132 as has been described.

With repeated fillings and drainings of the basin 103, the level of liquid in the fill tank 124 decreases with a corresponding increase in the level of the liquid in the drain tank 126. The height of the liquid in each tank 124 and 126 may be tracked by a conventional level sensor such as a mechanical float or a capacitive type level sensor.

Preferably no additional level sensor is employed. The volume of liquid for each use of the densitometer 100 is known and defined by the fill level of the heating chamber 132. The microprocessor 38 may therefore track the level of liquid remaining in the supply tank 124 by counting the number of times the basin 103 is filled to provide a signal to the user, via the display 18 or a remote video display terminal (not shown), indicating that the tanks 124 and 125 need to be refilled and drained respectively. This signal to the user is based on the number of times the basin 103 is filled and a calculation of the relative volumes of the heating chamber 132 and supply tank 124.

After completion of the use of the densitometer 100 for a period of time, the densitometer may be stored. In a storage mode, after both the supply tank 124 and drain tank 126 have been manually emptied, the microprocessor 38 instructs the pump/valve control circuit 160 to open both the fill valve 138 and the drain valve 148 and to run the pump 130. The drain valve 138 is opened slightly before the pump 130 is actuated to prevent the rush of air from causing liquid to flow out of the overflow port 134.

Referring now to FIGS. 10 and 15, the transducers 121 are inserted into the basin 103 through tubular sleeves 180 extending outward from the walls of the basin 103 at the curved pocket along an axes 212 of the opposed transducers 121. The tubular sleeves 180 define a circular bore in which the transducers 121 may be positioned. Each transducer 121 seals the sleeve 180 by compression of o-ring 182 positioned on the inner surface of the sleeve 180.

Although the transducers 121 fit tightly within the sleeves 180, their separation and alignment are determined not by the sleeves 180 but by an independent C-brace 184 comprising a first and second opposed arm 186 separated by a shank 188. A transducers 121 is attached to one end of each of the arms 186, the other ends of the arms 186 fitting against the shank 188.

The arms 186 are generally rectangular blocks transversely bored to receive the cylindrically shaped transducers 121 at one end and to hold them along axis 212. The other ends of the arms 186 provide planar faces for abutting the opposite ends of the block like shank 188, the abutting serving to hold the arms 186 opposed and parallel to each other.

Although the angles of the arms 186 with respect to the shank 188 are determined by the abutment of the planar faces of the arms 186 and the ends of the shank 188, alignment of the arms 186 with respect to the shank 188 is provided by dowel tubes 190 extending outward from each end of the shank 188 to fit tightly within corresponding bores in the first and second arm 186.

Cap screws 194 received in counterbored holes in the arms 186 pass through the arms 186, the dowel tubes 190 are received by threaded holes in the shank 188 to hold the arm 186 firmly attached to the shank 188. The dowel tubes 190 and surfaces between the arms 186 and shank 188 serve to provide extremely precise alignment and angulation of the transducers 121, and yet a joint that may be separated to permit removal of the transducers 121 from the densitometer 10 for replacement or repair.

Transducers 121 are matched and fitted to the arms 186 in a controlled factory environment to provide the necessary acoustic signal strength and reception. In the field, the shank 188 may be separated from one or both arms 186 by loosening of the cap screws 194 so as to allow the transducers 121 extending inward from the arms 186 to be fit within the sleeves 180. Proper alignment and angulation of the transducers is then assured by reattaching the arm or arms 186 removed from the shank 188 to the shank 188 to be tightened thereto by the cap screws 194. Thus, the alignment of the transducers is not dependent on the alignment of the sleeves 180 which may be molded of plastic and thus be of relatively low precision. Nor must alignment be tested while the transducers are in the sleeves 180 attached to the basin 103 but may be checked in a central controlled environment.

Flexible Bladder Embodiment

Referring now to FIGS. 16 and 17, in yet another embodiment of the present invention, the opposed transducers 121 are fitted with annular collars 200 which in turn are attached to flexible bladders 202 extending inward to the basin 103, each bladder 202 containing a liquid or semi-liquid coupling "gel" 204.

The bladders 202 serve to contain the gel about the face of the transducers 121 and conform to the left and right sides of a patient's heel 207, respectively, to provide a path between the transducers 121 and the soft tissue and bone of the heel 207 without intervening air. The bladder 202 further prevents the coupling material from direct contact with the heel to permit selection of the coupling gel 204 from a broader range of materials.

Compression of the bladders 202 against the heel 207, so as to provide the necessary coupling, is provided by a telescoping shank 181 shown in FIG. 16. In this alternative embodiment of the C-brace 184 of FIG. 15, the shank 188' has been cut into two portions 206 and 208 slidably connected together by dowel pins 210 to provide necessary motion of the transducers 121 inward along their axis to compress the bladders 202 against the heel 207. One end of each dowel pin 210 is press fit within bores in the 20 shank 188' parallel to the axis 212 of the opposed transducers in portion 206. The other ends of the dowel pins 210 slide within larger bores in portion 208 so that portions 208 and 206 may slide toward and away from each other parallel to the axis 212. With such motion, the attached arms 186 move towards and away from each other adjusting the separation of the transducers 121 between an open position for insertion of the heel 207 and a closed position of known separation and orientation where portions 208 and 206 abut.

Control of the separation is provided by means of cam pins 214 protruding from portions 206 and 208 on the side away from the extension of the arms 186 and generally perpendicular to the axis 212. These pins 214 are received by spiral shaped slots in a cam disk 217 fitting over the cam pins 214. The disk includes radially extending lever 218 whose motion rotates the disk causing the cam pins 214 within the slots 215 to be moved together or apart depending on motion of lever 218.

Thus, the transducers 121 may be moved apart together with the bladders 202 for insertion of the heel 207 into the basin 103. Once the heel is in place, motion of the lever 218 closes the transducers 121 to a predetermined fixed separation compressing the bladders 202 snugly against the sides of the heel 207. The elasticity of the bladder filled with coupling gel 204 provides an expanding force against the heel 207 to closely conform the surface of the bladder 202 to the heel 207.

Cancellation of Heel Width Variations

Figure 18:
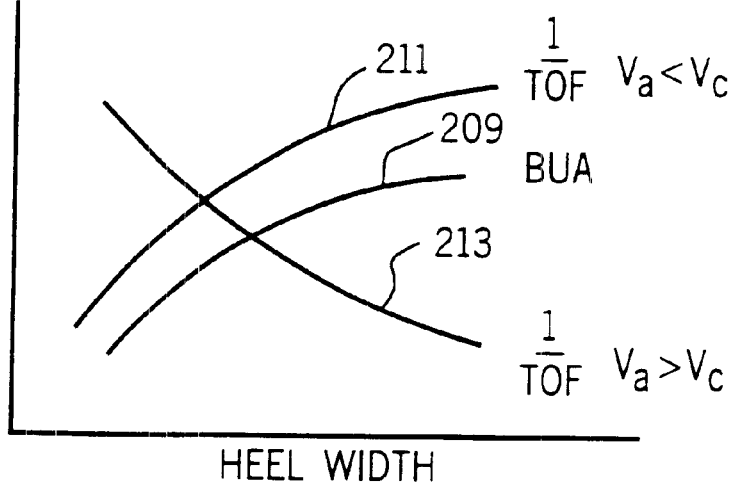
FIG. 18 is a plot of the inverse of time of flight (TOF) for two bone conditions and broadband ultrasonic attenuation (BUA) as a function of heel width showing their opposite functional dependencies.

Referring to FIGS. 17 and 18, generally the thicker the calcaneus 216 of the heel 207, the greater the attenuation of an acoustic signal passing through the heel 207 between transducers 121. Correspondingly, with greater attenuation, the slope of attenuation as a function of frequency, generally termed broadband ultrasonic attenuation (BUA) also increases as shown generally in FIG. 18 by plot 209. This assumes generally that the coupling medium 204 is of low or essentially constant attenuation as a function of frequency. Greater BUA is generally correlated to higher bone quality.

For constant heel thickness, lower TOF (faster sound speed) corresponds generally to higher bone quality. The time of flight (TOF) of an acoustic pulse between the transducers 121 will be proportional to the time of flight of the acoustic pulse through regions A of FIG. 17 comprising the path length through coupling gel 204, regions B comprising the path length through soft tissue of the heel 207 surrounding the calcaneus 216, and region C comprising the path length through the heel bone or calcaneus 216. Thus, $$TOF = \frac{1}{V_A}A + \frac{1}{V_B}B + \frac{1}{V_C}C \qquad (2)$$

where $V_A$, $V_B$, and $V_C$ are the average speed of sound through the coupling gel, soft tissue and bone respectively and A, B, C are the path lengths through these same materials. Provided that the separation between the transducers 121 is a constant value K, then time of flight will equal:

$$TOF = \frac{1}{V_A}(K - C - B) + \frac{1}{V_B}B + \frac{1}{V_C}C \qquad (3)$$

The change in time of flight as a function the thickness of the bone C (the derivative of TOF with respect to C) will thus generally be equal to:

$$\frac{1}{V_C} - \frac{1}{V_A}.$$

Referring now to FIG. 18, if the velocity of sound through the coupling medium 204 is greater than that through the bone being measured $$\left(V_A > V_C, \text{ or } \frac{1}{V_C} > \frac{1}{V_A}\right),$$

then the functional relationship of TOF to heel width will be one of increasing as the heel becomes wider (indicated at plot 213 showing values of 1/TOF). On the other hand, if the velocity of sound through the coupling medium 204 is less than that through the bone being measured $$\left(V_C > V_A, \text{ but } \frac{1}{V_A} > \frac{1}{V_C}\right),$$

then the functional relationship of TOF to heel width will be one of decreasing as the heel becomes wider (indicated at plot 211 showing values of 1/TOF).

A combined bone health figure may be obtained by combining BUA and 1/TOF measurements (1/TOF because BUA increases but TOF decreases with healthier bone). Further, if (1) the conditions of ultrasonic propagation are adjusted so that the slope of 1/TOF with heel width is opposite in sign to the slope of BUA with heel width (i.e., $V_A > V_C$) and (2) the BUA and 1/TOF measurements are weighted with respect to each other so that the opposite slopes of the BUA and 1/TOF are equal, then the algebraic combination of the BUA and TOF, through addition for example, will produce a bone quality measurement substantially independent of heel width for a range of bone qualities.

This can be intuitively understood by noting that as the heel gets wider, it displaces some of the coupling gel 204 from between the heel 207 and each transducer 121, and by displacing material that conducts sound slower than the bone being measured increasing the total speed with which the sound is conducted.

Note that a similar effect may be obtained by proper scaling and combination of BUA and TOF by multiplication and that other functions of attenuation and TOF could be used taking advantage of their functional independence and their functional dependence in part on heel width.

Figure 19:
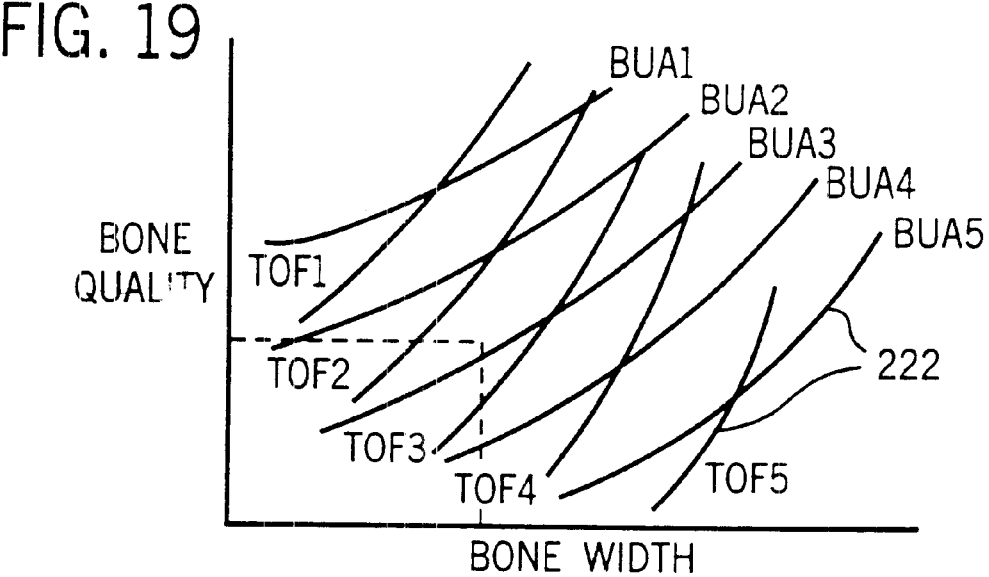
FIG. 19 is a plot of bone quality versus bone width as might be obtained from empirical measurement of multiple bone phantoms and as may be used to eliminate bone width effects in the ultrasonic assessment of bone quality.

Referring now to FIG. 19, generally BUA and TOF are functionally related to both bone quality and bone width. It should be possible, therefore, to solve the equations governing these relationships for bone quality alone and thus to eliminate the effect of the common variable of heel width. With such an approach, the variable of heel width is eliminated not just for a portion but through the entire range of bone measurement provided that the coupling medium is different from the bone being measured so that there will be a width effect in both BUA and TOF measurements.

Approximations of the algebraic relationships describing the functional dependence of BUA and TOF on bone quality and bone width, can be obtained through the construction of a set of bone phantoms of different widths and bone qualities when using a particular coupling gel. Generally, for each value of BUA or TOF the data will describe a curve 222 linking that value with different combinations of bone quality and bone width. This data may be placed in a look-up table in the memory of the microprocessor of the densitometer as has been previously described.

After BUA and TOF values are determined, the data of the look-up table (comprising many bone quality and bone width pairs for each of the determined BUA and TOF values) are scanned to find a bone quality and width data pair for the BUA value matching a bone quality and width data pair for the TOF value. This is equivalent to finding the intersection of the two curves 222 associated with the measured BUA and TOF values. The matching bone quality values of the data base will give a bone quality having little or no bone width influence. This value may be displayed to the clinician. It is noted that the previously described technique of summing weighted values of BUA and 1/TOF is but a specialized form of this process of algebraic solution.

Alternatively, a matching bone width value can be identified, being the width of the measured heel, and used to correct either of the BUA or TOF values for display to the clinician in circumstances where BUA or TOF values are preferred for diagnosis.

This ability to cancel out heel width effects will work only for bone qualities where the relationship between the coupling gel 204 and the calcaneus 216 are such as to provide a functional dependence on heel width. Cancellation will not occur, for example, if the density of the calcaneus 216 being measured is substantially equal to the sound speed of the coupling gel 204 and thus where displacement of the coupling gel by similar bone will have no net effect on time of flight. Thus the coupling gel must be properly selected. In this case, materials having higher sound speed may be selected for the coupling material. The difference between the coupling gel and the bone being measured will influence the accuracy of the cancellation of heel width effects.

Moderating this desire to improve heel width effects is the importance of keeping the coupling gel 204 close to the acoustic properties of the soft tissue of the heel 207 both to prevent reflection by impedance mismatch and to prevent variations in the thickness of the soft tissue in regions B from adding additional uncertainty to the measurement. The coupling medium of water provides good matching to the soft tissue of the heel 207 and has a sound velocity very close to bone and some osteoporotic conditions. Weighting of the attenuation and propagation time may be made for water.

Although the preferred embodiment of the invention contemplates display of a bone quality value or corrected TOF or BUA values, it will be recognized that the same effect might be had by displaying uncorrected BUA or TOF values on a chart and establishing a threshold for healthy or weak bone based on the corrections determined as above.

Ultrasonic Densitometer with Scannable Focus

Referring now to FIG. 20, a receiving transducer array 300, similar to array 21 described with respect to FIG. 1, may be positioned adjacent to the heel of a patient (not shown) to receive an ultrasonic wave 410 along axis 304. The receiving transducer array 300 includes a piezoelectric sheet 302 of substantially square outline positioned normal to the transmission axis 304 and is divided into transducer elements 400 as will be described, each which receives a different portion of the ultrasonic wave 410 after passage through the heel.

Figure 23:
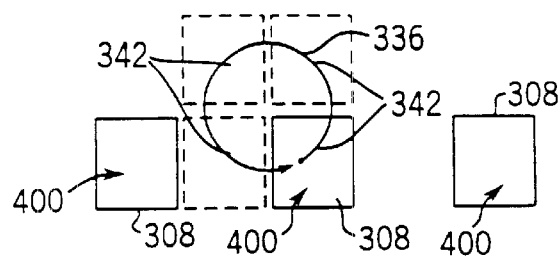
FIG. 23 is a detailed view of the face of the detector showing its displacement by the driving mechanism of FIG. 20.

The piezoelectric sheet 302 may be constructed of polyvinylidene fluoride and has a front face 306 covered with a grid of interconnected square electrodes 308 deposited on the front face by vacuum metallization. These square electrodes 308 are arranged at the interstices of a rectangular grid to fall in rectilinear rows and columns. Referring also to FIG. 23, each square electrode 308 is spaced from its neighboring electrodes 308 by approximately its width. These square electrodes 308 are connected together by metallized traces (not shown) and to a common voltage reference by means of a lead 310.

In the manufacture of the piezoelectric sheet 302, the polyvinylidene sheet is polarized to create its piezoelectric properties by heating and cooling the sheet in the presence of a polarizing electrical field according to methods generally understood in the art. In the present invention, this polarizing field is applied only to the area under the square electrodes 308 so that only this material is piezoelectric and the material between square electrodes 308 has reduced or no piezoelectric properties. As will be understood below, this selective polarization of the piezoelectric sheet 302 provides improved spatial selectivity in distinguishing between acoustic signals received at different areas on the piezoelectric sheet.

Referring now to FIG. 22, opposite each electrode 308 on the back side of the piezoelectric sheet 302 furthest from the source of the ultrasonic wave 410 is a second electrode 312 having substantially the same dimensions as the square electrodes 308 and aligned with corresponding square electrodes 308 along transmission axis 304.

Referring to FIGS. 20 and 21, a connector board 318 of areal dimension substantially equal to the piezoelectric sheet 302 has, extending from its front surface, a number of conductive pins 320 corresponding to the pads 316 in number and location. The pins 320 are stake-type terminals mounted to an epoxy glass printed circuit board 322 of a type well known to those of ordinary skill in the art. Each conductive pin 320 is connected directly to a preamplifer and then by means of printed circuit traces to a multiplexer 325 to a reduced number of control and data lines 324 which may be connected to the microprocessor 38 of the densitometer through an A to D converter 42 described previously with respect to FIG. 1 and as is well understood in the art. The preamplifers allow grounding of those electrodes 312 not active during scanning to reduce cross-talk between electrodes 312.

As shown in FIG. 21, the pins 320 of the connector board 318 are electrically connected to electrodes 312 on the back surface of the piezoelectric sheet 302 by means of a strip of thin (0.0005") Mylar 316 having conductive fingers 314 on its surfaces. The conductive fingers 314 on the front and rear surfaces of the Mylar strip 316 are in electrical communication through a plated-through hole 313 in the Mylar 316 connecting the fingers 314.

Each conductive pin 320 is attached to a conductive finger 314 at one edge of the Mylar strip 316 at the rear of the Mylar strip 316 (according to the direction of the acoustic wave) by means of an anisotropically conductive adhesive film 315 providing electrical conduction only along its thinnest dimension, thus from pin 320 to finger 314 but not between fingers 314 or pins 320. Anisotropically conductive film suitable for this purpose is commercially available from 3M corporation of Minnesota under the trade name of 3M Z-Axis Adhesive Film.

The other end of each plated finger 314 on the front of the Mylar strip 316 is then connected to an electrode 312 by a second layer of anisotropically conductive adhesive film 317. The Mylar strip 316 flexes to allows the pins 320 to be spaced away from the electrode 312 to reduce reflections off the pins 320 such as may cause spurious signals at the piezoelectric sheet 302. The Mylar strip 316 and conductive fingers 314 are essentially transparent to the acoustic wave.

Referring to FIG. 22, the Mylar strips 316 and adhesive film 315 and 317 allow rapid assembly of the transducer 300. A single layer of conductive film 317 (not shown in FIG. 22) may be applied over the entire rear surface of the piezoelectric sheet 302 and electrodes 312. Next a plurality of overlapping Mylar strips 316 may be laid down upon this surface, each Mylar strip 316 extending laterally across the piezoelectric sheet 302 with transversely extending conductive fingers 314 for each electrode 312 of one row of conductive electrode 312. The overlapping of the Mylar strips 316 ensures that only a front edge of each strip 316 adheres to the piezoelectric sheet 302. Guide holes 319 in the laterally extreme edges of the Mylar strips 316 fit into pins in a jig (not shown) to ensure alignment of fingers 314 with electrodes 312.

Next, a second layer of the anisotropically conductive adhesive film 315 is placed on the rear surfaces of the overlapping Mylar strips 316 and the conductive pins 320 pressed down on this film 315, aligned with the other ends of the conductive fingers 314 to attach to their respective fingers 314. The conductive pins 320 are then raised and fixed in spaced apart relationship with the piezoelectric sheet 302, the Mylar strips 316 flexing to accommodate this displacement.

The ultrasonic wave 410 passing through portions of the piezoelectric sheet 302 between electrodes 308 and 312 may thereby be measured at a number of points over the surface of the piezoelectric sheet by the electric signals generated and collected by electrodes 308 and 312 according to multiplexing methods well known in the art. Each electrode pair 308 and 312 provides an independent signal of the acoustic energy passing through the area of the piezoelectric sheet 302 embraced by the electrode pair.

A protective frame 325 encloses the piezoelectric sheet 302 and connector board 318 protecting them from direct contact with water of the basin 103 shown in FIGS. 10 and 15 into which the receiving transducer array 300 may be placed. The frame 325 holds on its front face an acoustically transparent and flexible material 326 such as a Teflon film so that the ultrasonic wave 410 may pass into the frame to reach the piezoelectric sheet 302.

The above described array may be used either to receive or transmit acoustic waves and is not limited to use in the medical area but may provide an inexpensive and rugged industrial acoustic array useful for a variety of purposes including industrial ultrasonic imaging and the construction of high frequency synthetic aperture microphones.

Positioned behind the frame 325 is an electric motor 328 driving a central gear 330 about an axis aligned with transmission axis 304 and approximately centered within the frame 325. The central gear 330 in turn engages two diagonally opposed planet gears 332 also turning about axes aligned with the transmission axis. Each planet gear 332 has a rod 334 extending forwardly from a front face of the planet gear 332 but offset from the planet gear's axis to move in an orbit 336 thereabout. The orbit 336 has a diameter approximately equal to the spacing between electrodes 308.

The rods 334 engage corresponding sockets 338 on the back side of the frame 325 at its opposed corners. Thus activation of the motor 328 causes the piezoelectric sheet 302 and connector board 318 to follow the orbit 336 while maintaining the rows and columns of detector elements 400 in horizontal and vertical alignment, respectively.

Referring now to FIG. 23, a sampling of the signals from the detector elements 400 may be made at four points 342 in the orbit 336 at which each electrode 308 is first at a starting position, and then is moved half the inter-electrode spacing upward, leftward, or upward and leftward. The effect of this motion of the detector elements 400 is to double the spatial resolution of the received acoustic signals without increasing the amount of wiring or the number of detector elements 400. The sampling of acoustic energy at each of the points 342 is stored in the memory of the microprocessor and can be independently processed to derive attenuation, BUA or time of flight measurements or a combination of these measurements. These measurements are then converted to an intensity value of an image so that each pixel of the image has an intensity value proportional to the measured parameter. A clinician viewing the image thus obtains not merely an image of the bone, but an image that indicates bone quality at its various points.

A transmitting ultrasonic transducer 408 is positioned opposite the receiving transducer array 300 from the heel 207 and produces a generally planar ultrasonic wave 410 passing into the heel. Generally, the acoustic signal received by each transducer element 400 will have arrived from many points of the heel.

Figure 24:
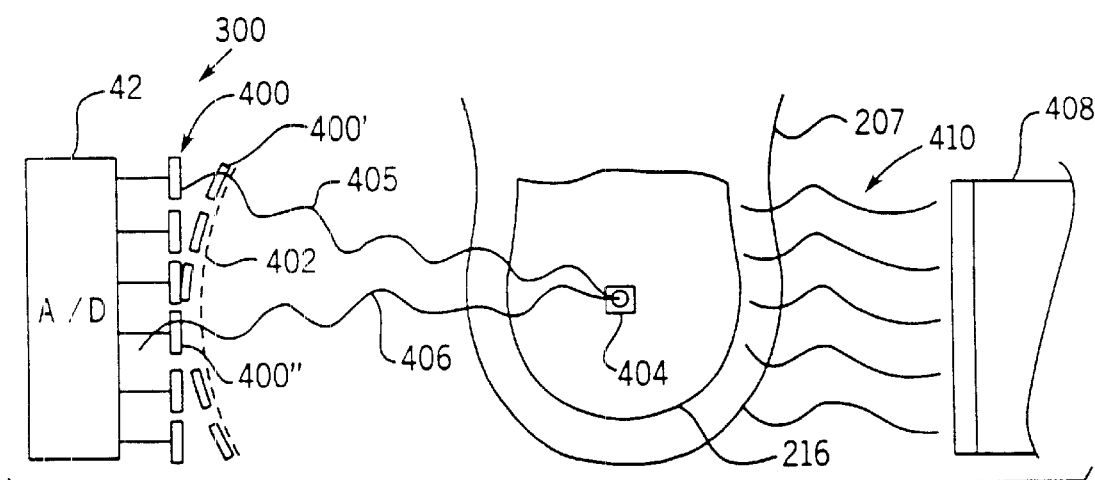
FIG. 24 is a figure similar to that of FIG. 17 showing use of the detector array to provide focused reception at a point within a patient's heel.

Referring now to FIG. 24, if the transducer elements 400 were focused as indicated by depicted transducer elements 400' to follow a hemisphere 402 having a radius and hence focus at a particular volume element or voxel 404 within the heel, acoustic signals from other voxels could be canceled providing greater selectivity in the measurement. In this focusing of the transducer elements 400', the signals from each of the elements 400' are summed together. Constructive and destructive interference of ultrasonic waves 410 from the heel 207 serve to eliminate acoustic signals not flowing directly from focus volume element 404.

For example as depicted, two acoustic signals 405 and 406 from focus voxel 404 both crest at the location of a transducer element 400' as a result of the equidistance of each transducer element 400' from focus voxel 404. When the signals from transducer elements 400' are summed, the signal from focus voxel 404 will increase. In contrast, acoustic signals from other voxels not equidistant to transducer elements 400' will tend to cancel each other when summed and thus decrease.

The present invention does not curve the transducer elements 400 into a hemisphere but accomplishes the same effect while retaining the transducer element 400 in a planar array by delaying the signals received by the transducer elements 400 as one moves toward the centermost transducer element 400" so as to produce an effective hemispherical array. Like a hemispherical array, the center-most transducer elements 400 appear to receive the acoustic wave a little later than the transducer elements 400 at the edge of the receiving transducer array 300. By using a phase delay of the signals instead of curving the receiving array 300, the position of the focus voxel 404 at which the receiving array 300 is focused, may be scanned electrically as will be described. The signals from each of the transducer elements 400 are received by the A/D converter 42 and stored in memory. Phase shifting as described simply involves shifting the point at which one starts reading the stored signals.

Adjusting the phase of the acoustic signals received by each of the transducer elements 400 allows the location of the focus voxel 404 from which data is obtained to be scanned through the heel. The phase is simply adjusted so that the effective arrival time of an acoustic signal originating at the desired location is the same for each of the transducer elements 400.

Figure 25:
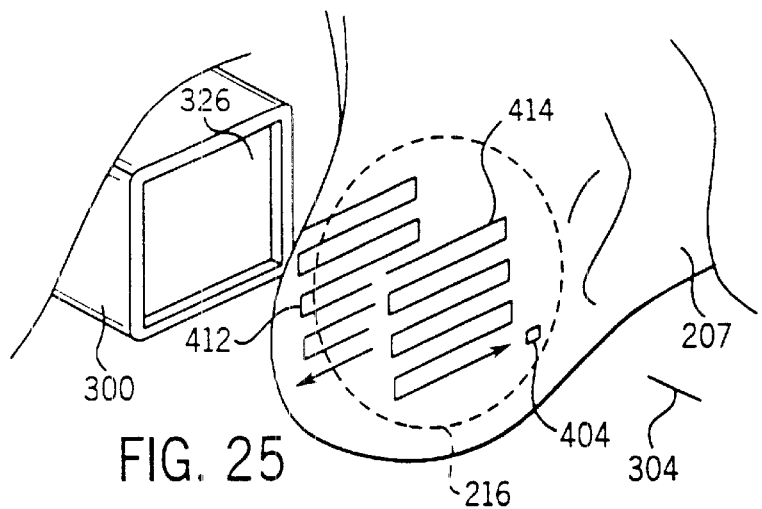
FIG. 25 is a perspective view in phantom of a patient's heel showing a raster scan pattern of a reception point within the heel to measure volumetric bone density variations within an inner and outer portion of the os calcis.

Referring now to FIG. 25, the location of focus voxel 404 may be moved in a first and second raster scan pattern 412 and 414 (as readings are taken over many ultrasonic pulses) to obtain separated planes of data normal to the transmission axis 304. The first plane of data 412 may, for example, be positioned near the outer edge of the os calcis 216 to measure the cortical bone quality while the second plane 414 may be placed in a centered position in the trabecular bone to obtain a somewhat different reading, both readings providing distinct data about the bone.

It will be understood that this same approach of scanning in different planes may be used to obtain a volume of data within the heel 207, in this case, the focus voxel 404 being moved to points on a three dimensional grid.

In another embodiment (not shown) the transmitting ultrasonic transducer may be an array and the phases of the ultrasonic signals transmitted by each of the elements of the array may be phased so as to focus on a particular voxel within the heel. In this case, the receiving array may be a single broad area detector or may also be an array focused on the same voxel for increased selectivity. The focus point of the transmitting and receiving arrays may also be shifted with respect to each other to investigate local sound transfer phenomenon. As before, the focal points of either array may be steered electrically by the microprocessor through a shifting of the phases of the transmitted and received signals. To collect data, each element of the transmit array may be energized individually while all receive elements of the receive array are read. This may be continued until each of the elements of the transmit array have been energized.

Figure 28:
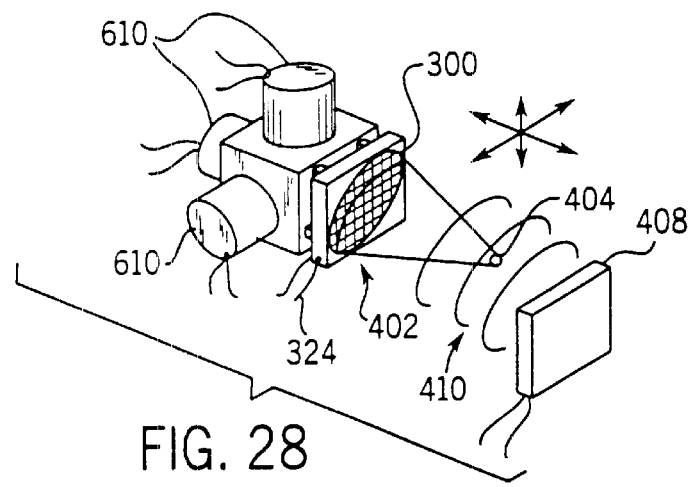
FIG. 28 is a perspective view of an embodiment of the invention using a fixed focus transducer array mechanically scanned to provide a plurality of spatially separated measurements.

Alternatively, referring to FIG. 28, the receiving array 300 may be actually formed so that its elements follow along the hemisphere 402 so as to have a fixed focus on focus voxel 404. Additional circuitry to effect the phase adjustment needed to focus the array is not needed in this case. The receiving array 300 is attached to an X-Y-Z table 600 providing motion in each of three Cartesian axes under the control of the microprocessor via stepper motors 610. At each different location of the table 600, data may be collected from focus voxel 404 to establish the data points on the three dimensional grid. The transmitting array 408 may be held stationary or may be moved with the scanning of the receiving array 300 and may be focused as well.

Figure 26:
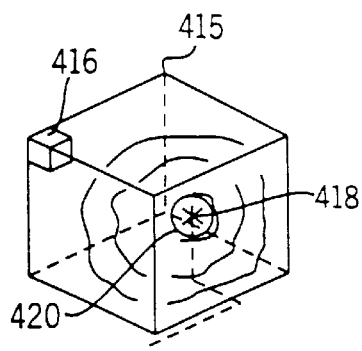
FIG. 26 is a schematic representation of a data cube collected in the scanning shown in FIG. 25 with isodensity lines used to locate a measurement region of interest.

Referring now to FIG. 26, such a data volume 415 may include a plurality of data voxels 416 each providing a measured member parameter for the bone or tissue at that point in the heel. A point of minimum bone density 418 may be found within this data volume 415 and used to identify a region of interest 420 which will serve as a standard region for measuring the bone density of the heel. This region may be automatically found after collection of the data volume 415 and only those voxels 416 within the region of interest 420 may be used for a displayed measurement. This automatic location of a region of interest 420 provides a much more precise bone characterization.

Acquiring a data volume 415 also provides the opportunity to use the extra data outside the region of interest 420 to ensure that the same region of interest 420 is measured in the patient's heel over a series of measurements made at different times. The data volume 415 may be stored in memory as a template that may be matched to subsequently acquired data volumes. The region of interest 420 spatially located with respect to the first template, may then be used as the region of interest for the subsequent data volumes aligned with that template to provide more repeatability in the measurement.

Figure 27:
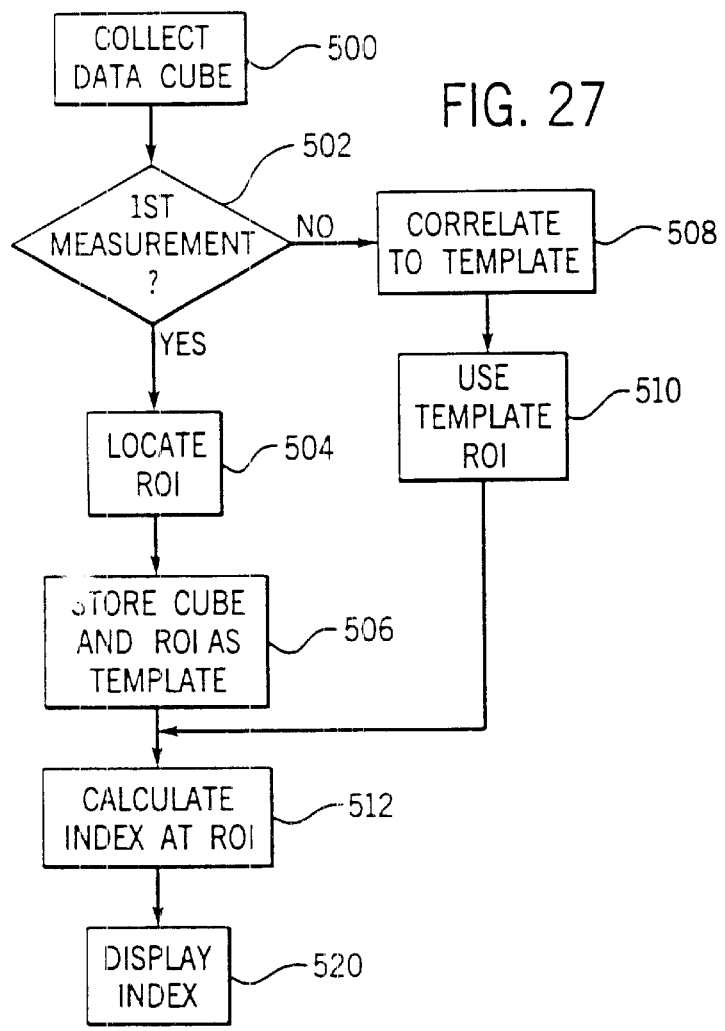
FIG. 27 is a flow chart of the operation of the present invention in locating a region of interest uniformly over several patient visits.

Referring now to FIG. 27 in such a template system in a first step 500, a collection of a data volume 415 within the heel is obtained. At decision block 502, if this is a first measurement of a particular patient, a region of interest 420 is identified at process block 504 from this data, as a predetermined volume centered about a point of minimum bone density 418 as described with respect to FIG. 26. At process block 506, the data volume is stored as a template along with the region of interest defined with respect to the data of the template.

Referring again to decision block 502 on a subsequent measurement of a patient, the program may proceed to process block 508 and the template previously established may be correlated to a new data volume 415 collected at process block 500. The correlation process involves shifting the relative locations of the two data volumes to minimize a difference between the values of each data voxel 416 of the data volumes. In most situations, this will accurately align the two data volumes so that corresponding voxels 416 of the two data volumes 415 measure identical points within the patient's heel. The region of interest 420 associated with the template is then transferred to the new data volume as it has been shifted into alignment with the template so that the identical region of interest may be measured in a patient even if the patient's foot has taken a different alignment with respect to the transducer array 300 and 408. This use of the template's region of interest 420 is indicated by process block 510.

At process block 512, an index is calculated at the region of interest 420 for the new data volume 415 being typically an average value of a bone parameter such as BUA or time of flight for the voxels 416 within the region of interest 420. This data is then displayed to the clinician at process block 520 as has been described.

It is specifically intended that the present invention not be specifically limited to the embodiments and illustrations contained herein, but embrace all such modified forms thereof as come within the scope of the following claims.

We claim:

1. A method of non-invasive and quantitative assessment of the status of bone tissue in vivo for at least one of the quantities, bone-mineral density, bone strength, bone fracture risk, bone architecture and bone quality comprising the steps of:

positioning a first and second transducer distant from the skin on opposite sides of said bone tissue to provide gaps therebetween allowing free insertion of said bone tissue unobstructed by the first and second transducers;

acoustically coupling a first transducer and a second transducer to a compliant medium bridging the gaps between the first and second transducers and the distant skin;

acoustically coupling the compliant medium to the distant skin on opposite sides of said bone tissue wherein one of said first and second transducers is a single-element transducer and another of said first and second transducers is an array transducer;

generating an ultrasound signal and directing said ultrasound signal from said first transducer to said second transducer through said bone tissue to obtain a bone-oriented output signal; and processing said bone-oriented output signal whereby an estimate of said at least one of the quantities, bone-mineral density, bone strength, bone fracture risk, bone architecture and bone quality is obtained.

2. The method of claim 1 wherein said processing step includes determining a transit time of said ultrasound signal through said bone tissue.

3. The method of claim 1 wherein said processing step includes determining a velocity of said ultrasound signal through said bone tissue.

4. The method of claim 1 wherein said processing step includes determining an attenuation slope associated with said ultrasound signal.

5. The method of claim 1 further comprising the step of independently directing said ultrasound signal from said first transducer to said second transducer through a medium with known acoustic properties and path length and free of said bone tissue to produce a reference electrical output signal and wherein said processing step includes establishing a set of bone-oriented parameters associated with said bone-oriented output signal and a set of reference parameters associated with said reference signal and subjecting said set of bone-oriented parameters and said set of reference parameters to comparative analysis.

6. The method of claim 1 wherein said second transducer is said array transducer.

7. A method of non-invasive and quantitative assessment of the status of bone tissue in vivo for at least one of the quantities, bone-mineral density, bone strength, bone fracture risk, bone architecture and bone quality comprising the steps of:

positioning a first and second transducer distant from the skin on opposite sides of said bone tissue to provide gaps therebetween allowing free insertion of said bone tissue unobstructed by the first and second transducers;

acoustically coupling a pair of transducers to a compliant medium bridging the gaps between the first and second transducers and the distant skin;

acoustically coupling the compliant medium to the distant skin on opposite sides of said bone tissue;

generating an ultrasound signal and directing said ultrasound signal from one transducer of said pair of transducers to another transducer of said pair of transducers through said bone tissue, to produce a bone-oriented electrical output signal;

independently directing said ultrasound signal from said one transducer to said another transducer through a medium with known acoustic properties and path length and free of said bone tissue to produce a reference electrical output signal;

establishing a set of bone-oriented parameters associated with said bone-oriented output signal and a set of reference parameters associated with said reference signal; and subjecting said set of bone-oriented parameters and said set of reference parameters to comparative analysis, whereby an estimate of said at least one of the quantities, bone-mineral density, bone strength, bone fracture risk, bone architecture and bone quality is obtained.

8. The method of claim 7 wherein said another transducer is an array transducer.

9. The method of claim 8 wherein said one transducer is an array transducer.

10. A method of non-invasive and quantitative assessment of the status of bone tissue in vivo for at least one of the quantities, bone-mineral density, bone strength, bone fracture risk, bone architecture and bone quality comprising the steps of:

(a) positioning a first and second transducer distant from the skin on opposite sides of said bone tissue to provide gaps therebetween allowing free insertion of said bone tissue unobstructed by the first and second transducers;

(b) acoustically coupling a pair of transducers to a compliant medium bridging the gaps between the first and second transducers and the distant skin;

(c) acoustically coupling the compliant medium to the distant skin on opposite sides of said bone tissue;

(d) generating an ultrasound signal and directing said ultrasound signal from one transducer of said pair of transducers to another transducer of said pair of transducers through said bone tissue, to produce a bone-oriented electrical output signal;

(e) repeating said step (d) a plurality of times to obtain a plurality of bone-oriented output signals;

(f) averaging said plurality of bone-oriented output signals to obtain an averaged bone-oriented output signal;

(g) independently directing said ultrasound signal from said one transducer to said another transducer through a medium with known acoustic properties and path length and free of said bone tissue to produce a reference electrical output signal;

(h) repeating said step (g) a plurality of times to obtain a plurality of reference signals;

(i) averaging said plurality of reference signals to obtain an averaged reference signal;

(j) establishing a set of bone-oriented parameters associated with said averaged bone-oriented output signal and a set of reference parameters associated with said averaged reference signal; and (k) subjecting said set of bone-oriented parameters and said set of reference parameters to comparative analysis whereby an estimate of said at least one of the quantities, bone-mineral density, bone strength, bone fracture risk, bone architecture and bone quality is obtained.

11. The method of claim 10 wherein said another transducer is an array transducer.

12. The method of claim 11 wherein said one transducer is an array transducer.

13. A method of non-invasive and quantitative assessment of the status of bone tissue in vivo for at least one of the quantities, bone-mineral density, bone strength, bone fracture risk, bone architecture and bone quality comprising the steps of:

(a) positioning a first and second transducer distant from the skin on opposite sides of said bone tissue to provide gaps therebetween allowing free insertion of said bone tissue unobstructed by the first and second transducers;

(b) acoustically coupling a first transducer and a second transducer to nearby skin on opposite sides of said bone tissue, wherein said second transducer is an array transducer;

(c) generating an ultrasound signal and directing said ultrasound signal from said first transducer to an element of said second transducer through said bone tissue to produce a bone-oriented electrical output signal;

(d) independently directing said ultrasound signal from said first transducer to said element of said second transducer through a medium with known acoustic properties and path length and free of said bone tissue to produce a reference electrical output signal;

(e) establishing a set of bone-oriented parameters associated with said bone-oriented output signal and a set of reference parameters associated with said reference signal;

(f) repeating said step (c), said step (d), and said step (e) at least one time wherein said ultrasound signal is directed in said step (c) and said step (d) from said first transducer to a previously unselected element of said second transducer to thereby create la plurality of sets $Q_s$ of bone-oriented parameters and a plurality of sets of reference parameters;

(g) evaluating said plurality of sets of bone-oriented parameters to locate an anatomical region; and (h) subjecting at least one set of said plurality of sets of bone-oriented parameters, said one set corresponding to said anatomical region, and at least one set of said plurality of sets of reference parameters to comparative analysis, whereby an estimate of said at least one of the quantities, bone-mineral density, bone strength, bone fracture risk, bone architecture and bone quality is obtained.

* * * * *